United States Patent [19]

Kahan et al.

[11] 4,282,322

[45] Aug. 4, 1981

[54] PROCESS FOR ENZYMATIC DEACYLATION OF ANTIBIOTICS

[75] Inventors: Jean S. Kahan; Frederick M. Kahan, both of Rahway, N.J.

[73] Assignee: Merck & Co., Inc., Rahway, N.J.

[21] Appl. No.: 70,082

[22] Filed: Aug. 27, 1979

Related U.S. Application Data

[63] Continuation of Ser. No. 893,848, Apr. 6, 1978, abandoned, which is a continuation of Ser. No. 734,584, Oct. 21, 1976, abandoned, which is a continuation-in-part of Ser. No. 634,560, Nov. 24, 1975, abandoned.

[51] Int. Cl.$^3$ .............................................. C12P 17/18
[52] U.S. Cl. ..................................... 435/119; 435/228; 435/822; 424/274; 435/34; 260/245.2 T
[58] Field of Search ................ 435/119, 121, 228, 230

[56] References Cited

U.S. PATENT DOCUMENTS

| | | | |
|---|---|---|---|
| 3,821,081 | 6/1974 | Abe et al. ..................... 435/228 X |
| 3,930,949 | 1/1976 | Kutzbach et al. ............... 435/230 X |
| 3,945,888 | 3/1976 | Takahashi et al. .............. 435/228 X |
| 3,950,357 | 4/1976 | Kahan et al. ................... 435/121 X |
| 4,229,534 | 10/1980 | Kahan et al. ........................ 435/119 |
| 4,235,967 | 11/1980 | Cassidy et al. ...................... 435/119 |

*Primary Examiner*—Lionel M. Shapiro
*Attorney, Agent, or Firm*—Frank M. Mahon; Hesna J. Pfeiffer

[57] ABSTRACT

This invention relates to two new antibiotics, desacetyl 890A$_1$ and desacetyl 890A$_3$, active against both gram-positive and gram-negative bacteria, which are produced by treating 890A$_1$ and 890A$_3$, respectively, with an N-acetylthienamycin amidohydrolase produced by a soil microorganism isolated by enrichment techniques. This invention also relates to the process whereby N-acetylated structures of the thienamycin class of antibiotics such as N-acetyl thienamycin can be enzymatically deacetylated.

11 Claims, No Drawings

PROCESS FOR ENZYMATIC DEACYLATION OF ANTIBIOTICS

This is a continuation of application Ser. No. 893,848, filed Apr. 6, 1978, now abandoned, which in turn is a Continuation of U.S. Ser. No. 734,584, filed Oct. 21, 1976, now abandoned, which in turn is a Continuation-in-part of U.S. Ser. No. 634,560, filed Nov. 24, 1975, now abandoned.

BACKGROUND OF THE INVENTION

The discovery of the remarkable antibiotic properties of penicillin stimulated great interest in this field which has resulted in the finding of many other valuable antibiotic substances such as: other penicillins, streptomycin, bacitracin, tetracyclines, chloramphenicol, erythromycins and the like. In general, the antibacterial activity of each of these antibiotics does not include certain clinically important pathogenic bacteria. For example, some are principally active against only gram-positive types of bacteria. Acquired resistance over the course of widespread use of existing antibiotics in the treatment of bacterial infection has caused a serious resistance problem to arise.

Accordingly, the deficiencies of the known antibiotics have stimulated further research to find other antibiotics which will be active against a wider range of pathogens as well as resistant strains of particular microorganisms.

SUMMARY OF THE INVENTION

This invention relates to two new antibiotic agents. More particularly, it is concerned with the new antibiotic substances, herein called desacetyl $890A_1$ and desacetyl $890A_3$. The invention encompasses the antibiotics in dilute forms, as crude concentrates and in pure forms.

It is an object of the present invention to provide the new and useful antibiotics which are highly effective in inhibiting the growth of various gram-negative and gram-positive microorganisms. Another object is to provide a process for the preparation of these novel antibiotic substances by the enzymatic deacetylation of the compounds $890A_1$ and $890A_3$. A further object of the present invention is to provide a process for the deacetylation of N-acetylthienamycin. Other objects will be apparent from the detailed description of this invention hereinafter provided.

The novel antibiotic substances of the present invention are produced by hydrolyzing the N-acetyl group of $890A_1$ and $890A_3$ using an amidohydrolase capable of hydrolyzing the N-acetyl group. A convenient source of an amidohydrolase with this capability is amidohydrolase producing strains of the microorganism *Protaminobacter ruber*. The particular enzyme produced by *Protaminobacter ruber* is N-acetylthienamycin amidohydrolase, a member of the sub-group of enzymes designated B.C. 3.5.1 according to the recommended enzyme nomenclature of the International Union of Pure and Applied Chemistry and the International Union of Biochemistry.

The microorganism capable of carrying out the deacetylation process was isolated from a soil sample and, based upon taxonomic studies, was identified as belonging to the species *Protaminobacter ruber* and has been designated MB-3528 in the culture collections of MERCK & CO., Inc., Rahway, N.J. A culture thereof has been placed on unrestricted permanent deposit with the culture collection of the Northern Regional Research Laboratories, Northern Utilization Research and Development Division, Agricultural Research Service, U.S. Department of Agriculture, Peoria, Ill., and has been assigned accession No. NRRL B-8143.

The morphological and cultural characteristics of *Protaminobacter ruber* NRRL B-8143 as well as carbon and nitrogen utilization and biochemical reactions are as follows:

*Morphology*—Cells are rod-shaped with rounded ends, $0.9–1.2 \times 2.3–4.6$ microns, occurring singly or in parts. Twenty-four and forty-eight hour cells stain gram-negative with a granular appearance. The granules, especially the polar granules, stain black with Sudan Black B. Cells are motile at 28° C., but motility is questionable at 37° C.

Cultural Characteristics—Nutrient agar colonies are at first thin, punctiform, semi-transparent and colorless, the becoming low convex, opaque, smooth, edge entire, somewhat dry in consistency and pigmented rose to rose-red.

Nutrient broth cultures are uniformly turbid with no pellicle.

Pigment production is not dependent on light or temperatures tested (28° C. and 37° C.). Pigment is soluble in acetone but insoluble in water or chloroform.

Growth on nutrient agar and brain-heart infusion agar under aerobic conditions is somewhat slow but good at 28° C.; growth is moderate to good but slower at 37° C.; there is not growth at 50° C.

UTILIZATION OF CARBON AND NITROGEN SOURCES

Using a basal salts medium with ammonium sulfate as nitrogen source, growth is good with arabinose, moderate with xylose, and poor with dextrose, fructose, mannose, rhamnose, lactose, maltose, sucrose, raffinose, cellulose, inositol and mannitol.

N-acetylethanolamine can be utilized as the sole carbon and nitrogen source.

No acid or gas is produced from dextrose or lactose in OF Basal Medium (Difco Laboratories, Detroit, Mich.) under aerobic or anaerobic conditions.

BIOCHEMICAL REACTIONS

The biochemical reactions are based on standard methods as described in *Manual of Microbiological Methods* edited by the Society of American Bacteriologists, McGrawHill Book Co., New York, 1957.

Catalase—positive
Oxidase—negative
Starch not hydrolyzed
Casein not hydrolyzed
Gelatin not liquefied
Litmus milk unchanged in consistency but becomes slightly alkaline after 7 days.
Indol—negative
$H_2S$—negative
Nitrates not reduced
Urease—positive
Lysine and ornithine decarboxylase—negative N-Acetylthienamycin, $890A_1$ and $890A_3$ are the terms applied to isomers of the antibiotic having the structure:

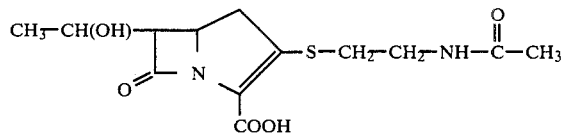

N-Acetylthienamycin, its description and process of production are set forth in the application of Kahan et al., U.S. Ser. No. 634,301, filed Nov. 21, 1975 now abandoned, which is herein incorporated by reference. 890A$_1$ and 890A$_3$, their description and processes of production are set forth in the application of Cassidy et al., U.S. Ser. No. 634,300, filed, filed on Nov. 21, 1975 now abandoned which is herein incorporated by reference.

The novel antibiotics of the present invention, desacetyl 890A$_1$ and desacetyl 890A$_3$ are isomers of the structural formula:

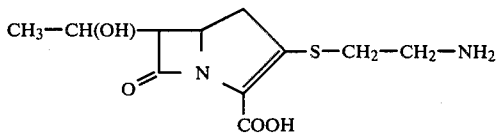

and are prepared by enzymatic hydrolysis of 890A$_1$ and 890A$_3$, respectively using an amidohydrolase present in species of genus Protaminobacter.

The novel process of the present invention relates to the cleavage of the N-acetyl group of the compounds of the structure:

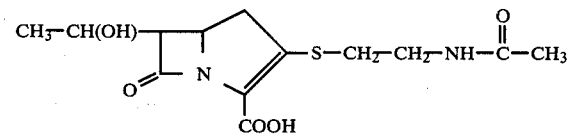

which comprises intimately contacting said compounds with an amidohydrolase capable of hydrolyzing the N-acetyl group. More specifically the process of the present invention provides for the N-deacetylation of N-acetylthienamycin, 890A$_1$ and 890A$_3$ by intimately contacting said compounds with the amidohydrolase, N-acetylthienamycin amidohydrolase.

An unexpected homology between N-acetylethanolamine and N-acetylthienamycin is set forth, whereby extracts of microorganisms with the hitherto undescribed enzyme, N-acetylethanolamine amidohydrolase, are in many cases able to hydrolyze N-acetylthienamycin. Furthermore, amidohydrolases capable of hydrolyzing N-acetylthienamycin are also found to be active in the conversion of antibiotics 890A$_1$ and 890A$_3$ to their novel desacetyl forms. Another novel aspect of the present invention relates to the process for obtaining such microorganisms, wherein the process comprises selecting the strains capable of using N-acetylethanolamine for growth and then testing these microorganisms for the presence of N-acetylthienamycin amidohydrolase.

The antibiotic thienamycin, obtained by the novel N-deacetylation of N-acetylthienamycin is a useful antibiotic. Its description, method of production and utility are set forth in the application of Kahan et al., U.S. Ser. No. 526,992, filed Nov. 25, 1974 U.S. Pat. No. 3,950,357 which is incorporated herein by reference. The antibiotics desacetyl 890A$_1$ and 890A$_3$ are novel and useful antibiotics.

One aspect of the present invention is the novel deacetylation of N-acetylthienamycin. There are two sources of N-acetylthienamycin. N-acetylthienamycin is prepared by the fermentation of broth with the microorganism *Streptomyces cattleya* NRRL 8057. This microorganism also produces thienamycin which may be chemically N-acetylated.

Based upon extensive taxonomic studies, *Streptomyces cattleya*, isolated from a soil sample, was identified as an actinomycete and has been designated MA-4297 in the culture collection of MERCK & CO., Inc., Rahway, N.J. A culture thereof has been placed on unrestricted permanent deposit with the culture collection of the Northern Regional Research Laboratories, Northern Utilization Research and Development Division, Agricultural Research Service, U.S. Department of Agriculture, Peoria, Ill., and has been assigned accession No. NRRL 8057.

The classification keys for the genus Streptomyces and the culture descriptions of Streptomyces species found in Bergey's *Manual of Determinative Bacteriology* (7th Edition, 1957) and in *The Actinomycetes*, Vol. II (1961) by S. A. Waksman and in "Cooperative Descriptions of Type Cultures of Streptomyces" by E. B. Shirling and D. Gottlieb, *International Journal of Systematic Bacteriology*, 18, 69–189 (1968), 18, 279–392 (1968), 19, 391–512 (1969) and 22, 265–394 (1972) were searched for a Streptomyces species having morphological and cultural characteristics similar to those of MA-4297. In these aforementioned classical references, no Streptomyces species is described to have the orchid pigmentation of the aerial mycelium, the morphological characteristics and the absence of diffusible pigment which together comprise distinctive characteristics of MA-4297. These considerations made the assignment of a new Streptomyces species justified and necessary.

The morphological and cultural characteristics of *Streptomyces cattleya* are set forth in the following table.

Morphology—Sporophores are compact spirals occurring as side and terminal branches on aerial mycelium. Spores are ellipsoidal to cylindrical in shape, $0.9\mu \times 1.2\mu$ in size, occurring in chains of more than 10.

CULTURAL

Tomato paste-oatmeal agar
  Vegetative growth—Reverse-tan, flat, spreading:
  Aerial mycelium—Orchid (10 gc) mixed with white;
  Soluble pigment—None.
Czapek Dox agar (sucrose nitrate agar)
  Vegetative growth—Colorless, flat, spreading;
  Aerial mycelium—Sparse, pinkish white;
  Soluble pigment—None.
Egg albumin agar
  Vegetative growth—Tan with grayed-orchid case, flat, spreading;
  Aerial mycelium—Orchid (10 gc) mixed with lighter shades of orchid and some white;
  Soluble pigment—None.
Glycerol asparagine agar
  Vegetative growth—Reverse-tan with gray-pink cast, flat, spreading;
  Aerial mycelium—Orchid (10 gc) mixed with some white;
  Soluble pigment—None.

Yeast extract-glucose+salts agar
  Vegetative growth—Tan with grayed pink cast;
  Aerial mycelium—Orchid (10 gc) mixed with pinkish-white;
  Soluble pigment—None.
Yeast extract-malt extract agar
  Vegetative growth—Tan;
  Aerial mycelium—Orchid (10 gc) mixed with pinkish-white;
  Soluble pigment—None.
Peptone-iron-yeast extract agar
  Vegetative growth—Tan;
  Aerial mycelium—None;
  Soluble pigment—Slight browning of medium;
  Melanin—Negative;
  $H_2S$ production—Negative.
Nutrient agar
  Vegetative growth—Light tan;
  Aerial mycelium—None;
  Soluble pigment—None.
Nutrient starch agar
  Vegetative growth—Cream to tan;
  Aerial mycelium—None;
  Soluble pigment—None;
  Hydrolysis of starch—Moderate.
Nutrient gelatin agar
  Vegetative growth—Cream-colored;
  Aerial mycelium—None;
  Soluble pigment—None;
  Liquefaction of gelatin—moderate.
Gelatin stabs
  Vegetative growth—Tan;
  Aerial mycelium—None;
  Soluble pigment—None;
  Liquefaction of gelatin—Moderate.
Potato plug
  Vegetative growth—Moderate, tan;
  Aerial mycelium—Sparse, grayish-pinkish-white;
  Soluble pigment—None.
Loeffler's Blood serum
  Vegetative growth—Cream-colored;
  Aerial mycelium—None;
  Soluble pigment—None;
  Liquefaction—None.
Skim milk agar
  Vegetative growth—Tan;
  Aerial mycelium—Sparse, whitish;
  Soluble pigment—Slight browning of medium;
  Hydrolysis of casein—Positive.
Litmus milk
  Vegetative growth—Tan to brown;
  Aerial mycelium-None;
  Color—No soluble pigment, litmus indicator becoming bluish;
  Coagulation and/or peptonization—Partial peptonization, becoming alkaline.
Skim milk
  Vegetative growth—Tan;
  Aerial mycelium—None;
  Soluble pigment—None;
  Coagulation and/or peptonization—Partial peptonization, becoming alkaline.
Tyrosine agar
  Vegetative growth—Tan;
  Aerial mycelium—Mixture of orchid (10 gc) and white;
  Soluble pigment—None;
  Decomposition of tyrosine—positive.

All of the readings reported above were taken after three weeks incubation at 28° C. unless noted otherwise. The pH of the media used in these studies was approximately neutral, namely, pH 6.8–7.2. The color designations used in the description are in accordance with the definitions of the *Color Harmony Manual,* 4th Edition (1956), Container Corporation of America, Chicago, Illinois.

*Streptomyces cattleya* was also tested for its ability to utilize or assimilate various carbohydrates. For this purpose, the microorganism was grown on basal synthetic medium (Pridham and Gottlieb) containing 1% of the carbohydrate at 28° C. for three weeks. The pH of the media employed in the study was approximately neutral (6.8–7.2). Table I shows the utilization of these carbohydrate sources by *Streptomyces cattleya:* +indicating good growth, ±poor growth, and -no growth on the particular carbohydrate.

TABLE I

| Glucose | + | Maltose | ± |
| --- | --- | --- | --- |
| Arabinose | − | Mannitol | + |
| Cellulose | − | Mannose | ± |
| Fructose | ± | Raffinose | − |
| Inositol | − | Rhamnose | − |
| Lactose | − | Sucrose | ± |
| Xylose | ± | | |

The amount of growth with change in temperature, the oxygen requirement and the effect on nitrate by the microorganism is as follows:
  Temperature range (Yeast extract-glucose+salts agar);
  28° C.—Good
  37° C.—Moderate
  50° C.—No growth
  Oxygen requirement (Stab culture in yeast extract-glucose+salts agar);
  Aerobic
  Nitrate reduction—Positive.

It is to be understood that the production of thienamycin is not limited to the organism *Streptomyces cattleya* or to organisms fully answering the above growth and microscopic characteristics which are given for illustrative purposes. In fact, it is desired and intended to include the use of mutants produced from the described organism by various means, such as X-radiation, ultraviolet radiation, nitrogen mustard, phage exposure and the like.

Thienamycin is produced during the aerobic fermentation of suitable aqueous nutrient media under controlled conditions via the inoculation with the organism, *Streptomyces cattleya.* Aqueous media, such as those employed for the production of other antibiotics are suitable for producing thienamycin. Such media contain sources of carbon, nitrogen and inorganic salts assimilable by the microorganism.

Another aspect of the present invention in the novel deacetylation of $890A_1$ and $890A_3$. $890A_1$ and $890A_3$ are prepared by fermentation of broth with the microorganism *Streptomyces flavogriseus* NRRL 8139. The material $890A_1$ may also be prepared by fermentation of *Streptomyces flavogriseus* NRRL 8140.

Based upon extensive taxonomic studies the strains of microorganisms were identified as belonging to the species *Streptomyces flavogriseus* and have been designated MA-4434a and MA-4600a in the culture collection of MERCK & CO., Inc., Rahway, N.J. A culture of each thereof has been placed on irrevocable permanent deposit with the culture collection of the Northern Regional Laboratories, Northern Utilization Research and Development Division, Agricultural Research Service, U.S. Department of Agriculture, Peoria, Ill., and have been assigned accession No. NRRL 8139 and 8140, respectively.

*Streptomyces flavogriseus* NRRL 8139 produces both antibiotics 890A$_1$ and 890A$_3$ which are isolated in substantially pure form from the fermentation broth. *Streptomyces flavogriseus* NRRL 8140 produces antibiotic 890A$_1$ without any detectable amount of 890A$_3$.

The morphological and cultural characteristics of *Streptomyces flavogriseus* NRRL 8139 are set forth in the following table.

*Morphology*—Sporophores are branching, straight to flexuous chains of spores, forming, tufts. Chains are more than 10 spores in length. Spores are spherical to oval-0.9μ × 1.2μ(970x).

CULTURAL CHARACTERISTICS

Oatmeal agar
    Vegetative growth—Reverse-yellowish tan, parchment-like growth;
    Aerial mycelium—Light gray edged with medium gray
    Soluble pigment—None.
Czapek Dox agar (sucrose nitrate agar)
    Vegetative growth—Reverse-brown edged with dark brown;
    Aerial mycelium—Medium gray, velvety;
    Soluble pigment—Slight browning of medium.
Egg albumin agar
    Vegetative growth—Reverse-yellowish tan edged with brown;
    Aerial mycelium—Medium gray mixed with yellowish gray (2 dc) and grayed yellow (2 db);
    Soluble pigment—Light yellowish tan.
Glycerol asparagine agar
    Vegetative growth—Reverse-yellowish tan, flat, spreading;
    Aerial mycelium—Velvety, light gray with a strong yellowish tone to gray (2 dc);
    Soluble pigment—None.
Inorganic salts-starch agar
    Vegetative growth—Reverse-brown;
    Aerial mycelium—Medium gray, velvety;
    Soluble pigment—Light yellowish-tan.
Yeast extract-dextrose+salts agar
    Vegetative growth—Reverse-brown edged with very dark brown;
    Aerial mycelium—Dark gray mixed with a light gray, velvety;
    Soluble pigment—None.
Yeast extract-malt extract agar
    Vegetative growth—Reverse-dark brown;
    Aerial mycelium—Dark grey, velvety;
    Soluble pigment—None.
Skim milk.agar
    Vegetative growth—Tan;
    Aerial mycelium—Sparse, grayish;
    Soluble pigment—Slight browning of medium;
    Hydrolysis of casein—Good.
Litmus milk
    Vegetative growth—Moderate growth ring, dark tan;
    Aerial mycelium—None;
    Color—Purple;
    Coagulation and/or peptonization—Complete peptonization; becoming alkaline, pH 8.2.
Skim milk
    Vegetative growth—Moderate growth ring, tan;
    Aerial mycelium—None;
    Soluble pigment—Tan;
    Coagulation and/or peptonization—Complete peptonization; becoming alkaline, pH 8.0.
Tyrosine agar
    Vegetative growth—Reverse-dark brown;
    Aerial mycelium—Dark gray;
    Soluble pigment—Slight browing of medium;
    Decomposition of tyrosine—None.
Peptone-iron-yeast extract agar
    Vegetative growth—Tan;
    Aerial mycelium—Sparse, grayish;
    soluble pigment—None;
    Melanin—None;
    H$_2$S production—None.
Nutrient agar
    Vegetative growth—Reverse-light grayish brown edged with darker gray-brown;
    Aerial mycelium—Light gray edged with dark gray;
    Soluble pigment—None.
Nutrient starch agar
    Vegetative growth—Tan edged with gray
    Aerial mycelium—Medium gray edged with dark gray;
    Soluble pigment—None;
    Hydrolysis of starch—Good
Nutrient gelatin agar
    Vegetative growth—Colorless edged with dark gray;
    Aerial mycelium—Grayish-white
    Soluble pigment—None;
    Liquefaction of gelatin—Good.
Potato plug
    Vegetative growth—Good growth, heavily wrinkled;
    Aerial mycelium—Gray to greenish-gray;
    Soluble pigment—Slight browning of medium.
Loeffler's Blood serum
    Vegetative growth—Cream-colored;
    Aerial mycelium—None;
    Soluble pigment—None;
    Liquefaction—None.
Gelatin stabs
    Vegetative growth—Cream-colored;
    Aerial mycolium—None;
    Soluble pigment—None;
    Liquefaction of gelatin—Good.

All of the readings reported above were taken after three weeks incubation at 28° C. unless noted otherwise. The pH of the media used in these studies was approximately neutral, namely, pH 6.8–7.2. The color designations used in the description are in accordance with the definitions of the *Color Harmony Manual*, 4th Edition (1958), Container Corporation of America, Chicago, Illinois.

*Streptomyces flavogriseus* NRRL 8139 was also tested for its ability to utilize or assimilate various carbohydrates. For this purpose, the microorganism was grown on basal synthetic medium (Pridham and Cottlieb) containing 1% of the carbohydrate at 28° C. for three weeks. The pH of the media employed in the study was approximately neutral (6.8–7.2). Table II shows the utilization of these carbohydrate sources by *Streptomyces flavouriseus* NRRL 8139, + indicating good growth, ± poor growth, and - no growth on the particular carbohydrate.

TABLE II

| | | | |
|---|---|---|---|
| Glucose | + | Maltose | + |
| Arabinose | + | Mannitol | + |
| Cellulose | − | Mannose | + |
| Fructose | + | Raffinose | − |
| Inositol | − | Rhamnose | + |
| Lactose | + | Sucrose | ± |
| Xylose | + | | |

The amount of growth with change in temperature and the oxygen requirement by the microorganism is as follows:

Temperature range (Yeast extract-dextrose+salts agar);
28° C.—Good
37° C.—Good vegetative growth; no aerial hyphae
50° C.—No growth
Oxygen requirement (Stab culture in yeast extract-dextrose+salts agar);
Aerobic The morphological and cultural characteristics of *Streptomyces flavogriseus* NRRL 8140 are set forth in the following table.

Morphology—Sporophores are branching, straight to flexuous chains of spores, forming tufts. Chains are more than 10 spores in length. Spores are spherical to oval—0.9μ×1.2μ (970x).

CULTURAL CHARACTERISTICS

Oatmeal agar
  Vegetative growth—Reverse-yellowish tan edged with dark brown;
  Aerial mycelium—Light gray edged with medium gray;
  Soluble pigment—None.
Czapek Dox agar (sucrose nitrate agar)
  Vegetative growth—Reverse-brown edged with dark brown;
  Aerial mycelium—Medium gray, velvety;
  Soluble pigment—None.
Egg albumin agar
  Vegetative growth—Reverse-grayish tan with sections of strong yellow tan;
Aerial mycelium—Sections of medium gray, grayish white and yellowish g. y (2dc); Soluble pigment—Very light tan.
Glycerol asparagine agar
  Vegetative growth—Yellowish tan;
  Aerial mycelium—Sparse, grayish;
  Soluble pigment—None.
Inorganic salts-starch agar
  Vegetative growth—Reverse-grayish cream;
  Aerial mycelium—Medium gray, velvety;
  Soluble pigment—None. Yeast extract-dextrose+-salts agar
  Vegetative growth—Reverse-dark brown;
  Aerial mycelium—Dark gray mixed with a light gray, velvety;
  Soluble pigment—None.
Yeast extract-malt extract agar
  Vegetative growth—Reverse-dark brown;
  Aerial mycelium—Dark gray, velvety;
  Soluble pigment—None.
Peptone-iron-yeast extract agar
  Vegetative growth—Tan;
  Aerial mycelium—None;
  Soluble pigment—None;
  Melanin—None;
  H₂S production—None.
Nutrient agar
  Vegetative growth—Light tan;
  Aerial mycelium—None.
  Soluble pigment—None.
Nutrient starch agar
  Vegetative growth—Cream-colored;
  Aerial mycelium—None;
  Soluble pigment—None;
  Hydrolysis of starch—Good.
Nutrient gelatin agar
  Vegetative growth—Cream-colored;
  Aerial mycelium—None;
  Soluble pigment—None;
  Liquefaction of gelatin—Good.
Gelatin stabs
  Vegetative growth—Tan;
  Aerial mycelium—None;
  Soluble pigment—None;
  Liquefaction of gelatin—Complete.
Skim milk agar
  Vegetative growth—Tan;
  Aerial mycelium—None;
  Soluble pigment—None;
  Hydrolysis of casein—Good.
Litmus milk
  Vegetative growth—Tan growth ring
  Aerial mycelium—None;
  Color—Brownish purple;
  Coagulation and/or peptonization—complete peptonization, becoming alkaline, pH 8.0.
Skim milk
  Vegetative growth—Tan, moderate growth ring;
  Aerial mycelium—None;
  Soluble pigment—Light brown;
  Coagulation and/or peptonization—Complete peptonization, becoming alkaline pH 8.5.
Potato plug
  Vegetative growth—Good, tan colored;
  Aerial mycelium—Very sparse, whitish;
  Soluble pigment—None.
Loeffler's Blood serum
  Vegetative growth—Cream-colored;
  Aerial mycelium—None;
  Soluble pigment—None;
  Liquefaction—None.
Tyrosine agar
  Vegetative growth—Tan;
  Aerial mycelium—None;
  Soluble pigment—Slight browning of medium;
  Decomposition of tyrosine—Very slight.

All of the readings reported above were taken after three weeks incubation at 28° C. unless noted otherwise. The pH of the media used in these studies was approximately neutral, namely pH 6.8-7.2. The color designations used in the description are in accordance with the definitions of the *Color Harmony Manual,* 4th Edition, 1958), Container Corporation of America, Chicago, Illinois.

*Streptomyces flavogriseus* NRRL 8140 was also tested for its ability to utilize or assimilate various carbohydrates. For this purpose, the microorganism was grown on basal synthetic medium (Pridham and Gottlieb) containing 1% of the carbohydrate at 28° C. for three weeks. The pH of the media employed in the study was approximately neutral (6.8-7.2) Table III shows the utilization of these carbohydrate sources by *Streptomyces flavogriscus* NRRL 8140+indicating good growth, ±poor growth, and −no growth on the particular carbohydrate.

TABLE III

| Glucose | + | Maltose | + |
|---------|---|---------|---|
| Arabinose | + | Mannitol | + |
| Cellulose | − | Mannose | + |
| Fructose | + | Raffinose | ± |
| Inositol | ± | Rhamnose | + |
| Lactose | + | Sucrose | ± |
| Xylose | + | | |

The amount of growth with change in temperature and the oxygen requirement by the microorganism is as follows:

Temperature range (Yeast extract-dextrose+salts agar);
28° C.—Good
37° C.—Moderate vegetative growth; no aerial hyphae
50° C.—No growth
Oxygen requirement (Stab culture in yeast extract-dextrose+salts agar);
Aerobic.

PHYSICAL AND CHEMICAL PROPERTIES OF ANTIBIOTICS $890A_1$ and $890A_3$

Properties of Antibiotic $890A_1$

Antibiotic $890A_1$ is an acidic substance which moves toward the positive pole on electrophoresis at neutral pH.

The sodium salt of antibiotic $890A_1$ is a white powder as lyophilized from aqueous solution, and is very soluble in water.

The ultraviolet absorbance spectrum has a λmax. at 299.5 nm and a λmin. at 242 nm. The E% at 300 nm of a solution of the sodium salt of antibiotic $890A_1$ in water at neutral pH is 208 for a pure sample; the ratio of absorbance values at 300 nm and 245 nm is 4.25 and the ratio $A_{300}/A_{210}$ is 1.41. More than 92% of the absorption at 300 nm may be eliminated by reaction with hydroxylamine, and a similar decrease is observed upon reaction with cysteine.

The circular dichroism spectrum of $890A_1$ displays a positive maximum at 290.5 nm with a specific ellipticity of 5270 degree-ml. per decimeter-gram, a point of zero ellipticity at 250 nm, and a negative minimum at 214 nm, with specific ellipticity of −10,910 degree-ml. per decimeter-gram.

The following table lists the 100 MHz-NMR signals for $890A_1$ sodium salt in $D_2O$ relative to the internal standard, sodium 2,2-dimethyl-2-silapentane-5-sulfonate, hereinafter referred to as DSS; chemical shifts are given in ppm and coupling constants in Hz; the apparent multiplicities are indicated.

1.35 (d, J=6.5); 1.98 (s); 3.63 (d of. d, J=5.2 and J=9.8); ∼4.02-4.26 (m); 3.18 (d of d, J=∼12 and J=10); 3.41 (t, J=6); 2.97 (d of t, J=3.5 and J=6).

PROPERTIES OF ANTIBIOTIC $890A_3$

Antibiotic $890_3$ is an acidic substance which moves to the positive pole on electrophoresis at neutral pH.

The sodium salt is a white powder when lyophilized from aqueous solution.

The ultraviolet absorbance spectrum has a maximum at 300.5 nm and a minimum at 243 nm. The E% at 300 nm of a solution of the sodium salt of antibiotic $890A_3$ in water at neutral pH is 375 for a pure sample; the ratio of absorbances at 300 nm and 245 nm is 3.54. More than 90% of the absorption at 300 nm may be eliminated by reaction with hydroxylamine; and a similar decrease is observed upon reaction with cysteine.

The circular dichroism spectrum of $890A_3$ has a positive maximum at 294 nm with a specific ellipticity of 9127 degrees-ml. per decimeter-gram, a point of zero ellipticity at 249 nm, and a specific ellipticity of −15,053 degrees-ml. per decimeter-gram at 220 nm.

The following table lists the 100 MHz-NMR signals for $890A_3$ sodium salt in $D_2O$ relative to the internal standard DSS; chemical shifts are given in ppm and coupling constants in Hz; the apparent multiplicities are indicated.

1.29 (d, J=6.5); 1.98 (s); 3.42 (d of d, J=5 and J=2.4); ∼4.01-4.28 (m); 3.14 (d of d, J=5 and J=9); 3.39 (t, J=6.5); 2.92 (d of t, J=∼4 and J=6).

MASS SPECTRAL ANALYSIS OF $890A_1$ and $890A_3$

The mass spectral data for $890A_1$ and $890A_3$ are obtained on trimethylsilyl derivatives prepared from ammonium salts of the antibiotics with bis-trimethylsilyltrifluoro acetamide in dimethyl formamide. Conversions of sodium salts of the antibiotics to the ammonium salts is carried out by using the ammonium salt of an acidic ion exchange resin.

Trimethyl-silylation of $890A_1$ and $390A_3$ results in three different derivatives: a di- and a tri-trimethylsilyl derivative (M.W.s 458 and 530, respectively) and a small amount of a tetra-trimethylsilyl derivative of a hydrolysed product (M.W. 620) wherein the β-lactam ring is open.

The values of the most important mass spectral fragment are given below:

di-trimethylsilyl derivative; 443.1495; 301.1034; 300.0962; 241.0590 and 86.0610.

tri-trimethylsilyl derivative: 515.1931; 373.1422 and 158.1000.

tetra-trimethylsilyl derivative (only low-resolution signal observed): 620 and 605.

Antibiotics $890A_1$ and $890A_3$ are isomers having a molecular structure as follows:

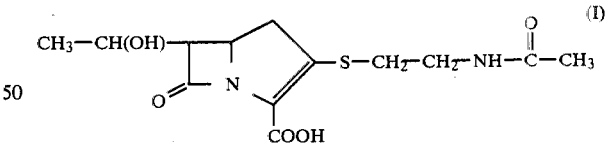

(I)

It is to be understood that the production of $890A_1$ and $890A_3$ is not limited to the organism, *Streptomyces flavogriseus* or to organisms fully answering the above growth and microscopic characteristics which are given for illustrative purposes. In fact, it is desired and intended to include the use of mutants produced from the described organism by various means, such as X-radiation, ultra-violet radiation, nitrogen mustard, phage exposure and the like.

$890A_1$ and $890A_3$ are produced during the aerobic fermentation, under controlled conditions, of suitable aqueous nutrient media inoculated with strains of the organism, *Streptomyces flavogriseus*. Aqueous media, such as those employed for the production of other antibiotics are suitable for producing $890A_1$ and $890A_3$.

Such media contain sources of carbon, nitrogen and inorganic salts assimilable by the microorganism.

Desacetyl 890A$_1$ and desacetyl 890A$_3$, the compounds of this invention are valuable antibiotics active against various gram-positive and gram-negtive bacteria and, accordingly, find utility in human and veterinary medicine. The compounds of this invention can be used as antibacterial drugs for treating infections caused by gram-positive or gram-negative bacteria, for example against susceptible strains of *Staphylococcus aureus, Proteus mirabilis, Escherichia coli, Klebsiella pneumoniae, Enterobacter cloacae* and *Pseudomonas aeruginosa*. The antibacterial materials of the invention may further be utilized as additives to animal feedingstuffs, for preserving foodstufs and as disinfectants. For example, they may be employed in aqueous compositions in concentrations ranging from 0.1 to 100 parts of antibiotic per million parts of solution or preferably in concentrations ranging from about 1 to about 10 parts of antibiotic per million parts of solution in order to destroy and inhibit the growth of harmful bacteria on medical and dental equipment and as bactericides in industrial applications, for example in water-based paints and in the white water of paper mills to inhibit the growth of deleterious bacteria.

The antibiotics of this invention may be used in any one of a variety of pharmaceutical preparations as the sole active ingredient or in combination either with one or more other antibiotics or with one or more pharmacologically active substances. As an example of the former, an aminocyclitol antibiotic such as gentamicin may be coadministered in order to minimize any chance that resistant organisms will emerge. As an example of the latter, diphenoxylate and atropine may be combined in dosage forms intended for the therapy of gastroenteritis. The antibiotics may be employed in capsule form or as tablets, powders or liquid solutions or as suspensions or elixirs. They may be administered orally, topically, intravenously or intramuscularly.

Tablets and capsules for oral administration may be in unit dose presentation form, and may contain conventional excipients such as binding agents, for example, syrup, acacia, gelatin, sorbitol, tragacanth, or polyvinylpyrrolidone; fillers, for example, lactose, sugar, maizestarch, calcium phosphate, sorbitol or glycine; lubricants, for example, magnesium stearate, talc, polyethylene glycol, silica; disintegrants, for example, potato starch or acceptable wetting agents such as sodium lauryl sulphate. The tablets may be coated according to methods well known in the art. Oral liquid preparations may be in the form of aqueous or oily suspension, solution, emulsions, syrups, elixirs, etc. or may be presented as a dry product, for reconstitution with water or other suitable vehicles before use. Such liquid preparations may contain conventional additives such as suspending agents, for example, sorbitol syrup, methyl cellulose, glucose/sugar syrup, gelatin, hydroxyethylcellulose, carboxymethyl cellulose, aluminum stearate gel or hydrogenated edible fats; emulsifying agents, for example lecithin, sorbitan monooleate or acacia; nonaqueous vehicles which may include edible oils, for example, almond oil, fractionated coconut oil, oily esters, propylene glycol, or ethyl alcohol; preservatives, for example methyl or propyl p-hydroxybenzoates or sorbic acid. Suppositories will contain conventional suppository bases, e.g. cocoa butter or other glyceride.

Compositions for injection may be presented in unit dose form in ampules, or in multidose containers with an added preservative. The compositions may take such forms as suspensions, solutions, emulsions in oily or aqueous vehicles, and may contain formulatory agents such as suspending, stabilizing and/or dispersing agents. Alternatively, the active ingredient may be in powder form for reconstitution with a suitable vehicle, e.g. sterile, pyrogen-free water, before use.

The compositions may also be prepared in suitable forms for absorption through the mucous membranes of the nose and throat or bronchial tissues and may conveniently take the form of powder or liquid sprays or inhalants, lozenges, throat paints, etc. For medication of the eyes or ears, the preparations may be presented as individual capsules, in liquid or semi-solid form, or may be used as drops etc. Topical application may be formulated in hydrophobic or hydrophilic bases as ointments, creams, lotions, paints, powders, etc.

Also, in addition to a carrier, the instant compositions may include other ingredients such as stabilizers, binders, antioxidants, preservatives, lubricators, suspending agents, viscosity agents or flavoring agents and the like.

In veterinary medicine, such as in the treatment of chickens, cows, sheep, pigs and the like, the compositions may, for example, be formulated as intramammary preparations in either long-acting or quick-release bases.

The dosage to be administered depends to a large extent upon the condition of the subject being treated, the weight of the host and the type of infection, the route and frequency of administration, the parenteral route being preferred for generalized infections and the oral route for intestinal infections.

In the treatment of bacterial infections in man, the compounds of this invention are administered orally or parenterally, in accordance with conventional procedures for antibiotic administration, in an amount of from about 2 to 600 mg./kg./day and preferably about 5 to 100 mg./kg./day in preferably divided dosage, e.g. three to four times a day. They may be administered in dosage units containing, for example, 25, 250, 330, 400 or 1000 mg. of active ingredient with suitable physiologically acceptable carriers or excipients. The dosage units are in the form of liquid preparations such as solutions or suspensions or as solids in tablets or capsules. It will, of course, be understood that the optimum dose in ny given instance will depend upon the type and severity of infection to be treated, and that smaller doses will be employed for pediatric use, all of such adjustments being within the skill of the practitioner in the field.

It is to be understood that the antibiotic thienamycin is also administered in the manner set forth above for the antibiotics desacetyl 890A$_1$ and desacetyl 890A$_3$.

ASSAY PROCEDURES FOR N-ACETYL THIENAMYCIN

I. Bioassay

Assays of antibacterial activity are run according to the following disc-diffusion method using either *Vibrio percolans* ATCC 8461 or *Staphylococcus aureus* ATCC 6538P as tester organism.

Plates containing *Vibrio percolans* ATCC 8461 are prepared as follows:

A lyophilized culture of *Vibrio percolans* ATCC 8461 is suspended in 15 ml. of a sterilized medium containing 8 g./l. of Difco Nutrient Broth and 2 g./l. of yeast extract in distilled water (hereinafter designated NBYE). The culture is incubated overnight on a rotary shaker at 28° C. This culture is used to inoculate the surface of slants containing 1.5% agar in NBYE, and the inoculated slants are incubated overnight at 28° C. and then stored in a refrigerator.

The refrigerated slants prepared from a single lyophilized culture are used for up to four weeks from their preparation, as follows: A loop of inoculum from the slant is dispersed in 50 ml. of NBYE contained in a 250 ml. Erlenmeyer flask. The culture is incubated overnight on a rotary shaker at 28° C., and is then diluted to a density giving 50% transmittance at 660 nm. A 33.2 ml. portion of this diluted culture is added to 1 liter of NBYE containing 15 g. of agar and maintained at 46° C. The inoculated agar-containing medium is poured into 100×15 mm. plastic petri dishes, 5 ml. per dish, chilled, and maintained at 2°–4° C. for up to 5 days before using.

Plates containing *Staphylococcus aureus* ATCC 6538P are prepared as follows:

An overnight growth of the assay organism, *Staphylococcus aureus* ATCC 6538P, in nutrient broth plus 0.2% yeast extract is diluted with nutrient broth plus 0.2% yeast extract to a suspension having 55% transmittance at a wavelength of 660 nm. This suspension is added to Difco nutrient agar supplemented with 2.0 g./l. Difco yeast extract at 47° C. to 48° C., to make a composition containing 33.2 ml. of the suspension per liter of agar. Five ml. of this suspension is poured into petri dishes of 85 mm. diameter, and these plates are chilled and held at 4° C. until used (5 day maximum).

Samples of antibiotic to be assayed are diluted to an appropriate concentration in phosphate buffer at ph 7. Filter paper discs, ¼ or ½ inch diameter, are dipped into the test solution and placed on the surface of the assay plate. The plates are incubated at 37° C. overnight, and the zone of inhibition is measured as mm. diameter. The zone of inhibition measured in mm. determines relative potencies.

II. Hydroxylamine-extinguishable absorbance

The proportion of absorbance measured at 301 nm which can be attributed to the antibiotic content in impure samples is determined by the selective extinction of this absorbance (with concomitant inactivation of antibiotic activity) upon reaction with dilute hydroxylamine.

Samples containing antibiotic to be tested are prepared in 0.01 M potassium phosphate buffer at pH 7 to have an initial $A_{301}$ between 0.1 and 1.0. Freshly prepared, neutralized hydroxylamine ($NH_2OH \cdot HCl$ plus NaOH to a final pH of 7) is added to a final concentration of 10 mM, and the reaction is allowed to progress at room temperature for at least 30 minutes. The resulting $A_{301}$ when subtracted from the initial reading (after correction for dilution by added reagent) yields the hydroxylamine-extinguishable absorbance. Solutions of pure N-acetylthienamycin show a hydroxylamine-extinguishable absorbance of 96.0%.

ASSAY PROCEDURES FOR THIENAMYCIN

I. Bioassay

Assays of antibacterial activity are run according to the following disc-diffusion procedure unless otherwise indicated. The assay plates are prepared in the following manner. An overnight growth of the assay organism, *Straphylococcus aureus* ATCC 6538P, in nutrient broth plus 0.2% yeast extract is diluted with nutrient broth plus 0.2% yeast extract to a suspension having 55% transmittance at a wavelength of 660 mµ. This suspension is added to Difco nutrient agar supplemented with 2.0 g./l. Difco yeast extract, at 47° C. to 48° C., to make a composition containing 33.2 ml. of the suspension per liter of agar. Five ml. of this suspension is poured into petri dishes of 85 mm. diameter, and these plates are chilled and held at 4° C. until used (5 day maximum).

Samples of the antibiotic to be assayed are diluted to an appropriate concentration in phosphate buffer at pH 7. Filter-paper discs, 0.5-inch in diameter, are dipped into the test solution and placed on the surface of the assay plate; two discs for each sample are normally placed on one plate opposite to one another. The plates are incubated overnight at 37° C. and the zone of inhibition is measured as mm. diameter. The zone of inhibition measured in mm. determines relative potencies or, when compared with a purified reference standard such as cephalothin, the potency of antibiotic in units/ml. The unit of activity is based on cephalothin standard solutions of 8, 4, 2 and 1 µg./ml. One unit is defined as the amount which calculates to produce the same inhibition as 1 µg. of cephalothin/ml. that zone of inhibition being between 16 and 21 mm. diameter.

II. Hydroxylamine-Extinguishable Absorbance

The proportion of absorbance measured at 297 nm which can be attributed to the antibiotic content in impure samples is determined by the selective extinction of this absorbance (with concomitant inactivation of antibiotic activity) upon reaction with dilute hydroxylamine.

Samples are prepared in 0.01 N potassium phosphate buffer at pH 7.0 to have an initial $A_{297}$ between 0.05 and 2.0. Freshly prepared, neutral hydroxylamine ($NH_2OH \cdot HCl$ plus NaOH to a final pH of 7) is added to a final concentration of 10 mM., and reaction is allowed to progress at room temperature for at least 30 min. The resulting $A_{297}$ when subtracted from the initial reading (after correction for dilution by added reagent) yields the hydroxylamine-extinguishable absorbance. Solutions of pure thienamycin show a hydroxylamine-extinguishable absorbance of 94.5%.

ASSAY PROCEDURES FOR 890A$_1$ and 890A$_3$

Bioassay

An agar plate disc-diffusion method is employed using either *Vibrio percolans* ATCC 8461 or *Salmonella gallinarum* MB-1287 as tester organism. A purified sample of antibiotic 890A$_1$ is used as standard.

Plates containing *Vibrio percolans* ATCC 8641 are prepared as follows:

A lyophilized culture of *Vibrio percolans* ATCC 8461 is suspended in 15 ml. of a sterilized medium containing 8 g./liter of Difco Nutrient Broth and 2 g./liter of yeast extract in distilled water "nutrient broth-yeast extract" (herein after designated NBYE). The culture is incubated overnight on a rotary shaker at 28° C. This culture is used to inoculate the surface of slants containing 1.5% agar in NBYE, and the inoculated slants are incubated overnight at 28° C., and then stored in a refrigerator.

The refrigerated slants prepared from a single lyophilized culture are used for up to four weeks from their preparation, as follows: A loop of inoculum from the slant is dispersed in 50 ml. of NBYE contained in a 250 ml. Erlenmeyer flask. The culture is incubated overnight on a rotary shaker at 28° C. and then diluted to a density giving 50% transmittance of 660 nm. A 33.2-ml. portion of this diluted culture is added to 1 liter of NBYE containing 15 g. of agar and maintained at 46° C.

The inoculated agar-containing medium is poured into 100×15 mm. plastic petri dishes, 5 ml. per dish, chilled, and maintained at 2°-4° C. for up to 5 days before using.

Plates containing *Salmonella gallinarum* MB-1287 are prepared as follows:

A sealed tube containing *Salmonella gallinarum* MB-1287 cells in skim milk, which had been frozen and lyophilized and sealed under vacuum, is opened and inoculated into 15 ml. of Brain Heart Infusion broth. The cells are allowed to grow without shaking at 37° C. overnight, and the culture is inoculated onto slants of 0.8% BBL Nutrient broth+0.2% Difco yeast extract+1.5% agar. After growth overnight at 37° C., a loop of the culture is transferred from the slant to a flask containing 50 ml. of 0.8% nutrient broth+0.2% yeast extract. The flask is shaken overnight, and 20 ml. of this culture is inoculated into one liter of 0.3% nutrient broth+0.2% yeast extract+1.5% agar which had been sterilized and cooled to 48° C. The inoculated NBYE agar is poured immediately into 100×15 mm. plastic petri dishes, 5 ml. per dish, and the plates are kept at 0°-3° C. until use.

Filter paper discs of one-half inch diameter are dipped into the solution to be assayed, and are placed on the agar. Alternatively, the discs may be loaded by pipetting one-tenth ml. of solution onto a dry disc, and then placing the disc on the agar. The diameter of the zone of inhibition is measured after appropriate incubation (9-18 hours at 37° C. for *Salmonella gallinarum* MB-1287 or 12-24 hours at 25° C. for *Vibrio percolans* ATCC 8461. If necessary, dilutions of the solutions to be assayed are made in 0.05 M potassium phosphate buffer, pH 7.4 "potassium phosphate buffer" (hereinafter referred to as KPB), or in deionized water.

Calculations of potencies proceed as follows: a slope is determined by measuring the zone diameters of a solution of antibiotic $890A_1$ or $890A_3$ and of a four-fold dilution (in KPB) of this solution. Two discs of each concentration are assayed on a single plate, and the average zone size at each concentration is determined. The slope is equal to one-half of the difference of the average zone sizes. Potencies are then calculated by the formula: Potency (units/ml.)=

$$\left(\frac{[D - D_s] \log 2}{\text{slope}}\right)$$

(Potency of Standard)×Dilution×10 where D is the average diameter of the zones formed by the unknown, $D_s$ is the average diameter of the standard zones, and "Dilution" is the degree to which the unknown was diluted before assay. If no standard is used, $D_s$ is assumed to be 25 mm. and (Potency of Standard) is taken as 1 unit/ml., when measured on *Vibrio percolans* ATCC 8461. Pure $890A_1$ is defined as having a potency of 250 units per hydroxylamine-extinguishable absorbance unit at 300 nm, when used as a standard. Accordingly, the potency of antibiotic $890A_3$ is 31 units per hydroxylamine-extinguishable absorbance unit at 300 nm.

For assays on *Salmonella gallinarum* MB-1287 plates, a slope is determined in the same way as on *Vibrio percolans* ATCC 8461 plates. When no standard is used, only relative potencies are calculated. If no slope is measured, a value of 2.3 mm. is assumed. The potency calculations proceed as with the *Vibrio percolans* ATCC 8461 assay. If no $890A_1$ standard is used, a control of penicillin G at 250 μg/ml. may be employed in order to verify that the sensitivity of the organisms is in the normal range.

II. Assay Procedure for Determining "890 Assay Units"

The conventional disc-plate assay procedure is employed and the discs are ½ inch in diameter. The routinely poured 10 ml./plate inoculated with *Vibrio percolans* (ATCC 8461) is used and the standard is cephaloridine. Four concentrations of cephaloridine constitute the standard—3.12, 6.25, 12.5 and 25 mcg. per ml. with the 12.5 mcg. per ml. as a reference solution. The zone diameters on a 5 ml. plate for the standard are as follows:

| Conc. (mcg./ml.) | Zone Diameter (mm.) |
|---|---|
| 3.12 | 16.8 |
| 6.25 | 22.3 |
| 12.5 | 25.0 |
| 25 | 29.6 |

A unit is defined as the amount of antibiotic-producing a 25 mm. zone of inhibition on a 5-ml. plate. Therefore, in this assay a concentration of 12.5 mcgg per ml. of cephaloridine is considered equivalent to 1 unit of 890A. Since the slope of the line for cephaloridine is 4.0, calculations of the potency of a sample are made using a slope of 4.0.

III. Hydroxylamine Reaction

Both antibiotics $890A_1$ and $890A_3$ react with hydroxylamine and produce a substance with greatly diminished absorbance at 300 nm. This provides the basis for a quantitative assay of the antibiotics $890A_1$ and $890A_3$.

The solution to be assayed is brought to 0.05 M in potassium phosphate, pH 7.4 by adding 1/20th volume of a solution containing 0.8 M $K_2HPO_4$ and 0.2 M $KH_2PO_4$. Then one-hundredth volume of 1 M hydroxylamine hydrochloride is added, and the absorbance at 300 nm is measured at intervals of one-half to two minutes. The reaction is conducted at 22°-28° C. First-order kinetics are assumed and a half-life is estimated from the absorbance decrease during the first ten minutes. From this half-life, the time is estimated beyond which no further absorbance decrease should be observed and observations are continued beyond that time. If no further decrease is observed beyond that time, the total absorbance decrease (correcting for dilution effect and absorbance of the hydroxylamine) is taken as the "Hydroxylamine-extinguishable absorbance at 300 nm ($HAEA_{300}$)". If absorbance decrease is observed beyond that time, the rate of background absorbance decrease is calculated, and the observed decrease at that time is corrected for background decrease, assuming that background decrease is linear with time. The corrected value is then recorded as the $HAEA_{300}$.

The number of $HAEA_{300}$ units is equal to the $HAEA_{300}$ multiplied by the volume in ml.

EXAMPLE 1

Method of Isolation of N-Acetylthienamycin amidohydrolase-producing Organisms A 1% (w/v) suspension of fertile lawn soil is prepared by suspending 1 gm. of lawn soil in 100 ml. sterile phosphate buffer-saline solution wherein the phosphate buffer-saline solution has the following composition:

| Phosphate Buffer-Saline Solution | |
|---|---|
| NaCl | 8.8 g. |
| 1M Phosphate Buffer, pH 7.5* | 10 ml. |
| Distilled H$_2$O | |

*1M Phosphate Buffer, pH 7.5
16 ml. 1M KH$_2$PO$_4$ are mixed with 84 ml. 1M K$_2$HPO$_4$. The pH of the phosphate buffer is adjusted to 7.5 by adding small quantities of either 1M KH$_2$PO$_4$ or 1M K$_2$HPO$_4$.

Aliquots of this 1% stock soil suspension are used to prepare 10×, 100× and 1,000× dilutions.

One-ml. portions of the stock suspension or 1-ml. portions of the 10×, 100× and 1,000× dilutions are added to 2-ml. portions of sterile, 1.0% agar solutions at 48° C. The mixtures are quickly poured over the surface of sterile petri dishes of 85 mm. diameter containing 20 ml. of Medium A. Medium A has the following composition:

| Medium A | |
|---|---|
| KH$_2$PO$_4$ | 3.0 g. |
| K$_2$HPO$_4$ | 7.0 g. |
| MgSO$_4$ | 0.1 g. |
| Distilled H$_2$O | 1000 ml. |
| N-Acetylethanolamine solution* | 8.5 ml. |

*N-Acetylethanolamine Solution
N-acetylethanolamine is diluted 10x in H$_2$O and membrane sterilized. This solution is added after autoclaving.

For solid media: Add 20 g. agar The petri dishes are incubated for 18 days at 28° C. Well-isolated colonies are picked and streaked on Medium B. Medium B has the following composition:

| Medium B | |
|---|---|
| Tomato paste | 40 g. |
| Ground oatmeal | 15 g. |
| Distilled H$_2$O | 1000 ml. |
| pH adjusted to 6 using NaOH | |

For solid media: add 20 g. agar Individual clones are selected and grown for 2 days at 28° C. on slants of Medium B.

A portion of the growth of the slants is used to inoculate a 250 ml. Erlenmeyer flask containing 50 ml. of Medium A; a 250 ml. Erlenmeyer flask containing 50 ml. supplemented Medium B (supplemented after autoclaving with 0.4 m. of a membrane-sterilized solution of N-acetylethanolamine diluted 10× with water); and a 250 ml. Erlenmeyer flask containing 50 ml. Medium C. Medium C has the following composition:

| Medium C | |
|---|---|
| Dextrose | 20 g. |
| Pharmamedia | 8 g. |
| Corn Steep Liquor (wet basis) | 5 g. |
| Distilled H$_2$O | 1000 ml. |
| pH adjusted to 7 with NaOH or HCl | |
| N-Acetylethanolamine solution* | 8.5 ml. |

*N-Acetylethanolamine Solution
N-acetylethanolamine is diluted 10x in H$_2$O and membrane sterilized. This solution is added after autoclaving.

The flasks are shaken at 23° C. on a 220 rpm (2" throw) shaker for 4 days. A 30-ml. portion from each flask is centrifuged for 15 minutes at 8,000 rpm. The supernatant portion is removed, leaving only enough to form a thick suspension of cells and media solids. Half of the suspension is subjected to ultrasonic disruption using a Branson Instrument Model LS-75 Sonifier with a ½ inch probe. The input power is set at position #4, and four successive 15 second cycles of irradition are used, while chilling the suspension in ice water during and between disruption. To test for the presence of N-acetylthienamycin amidohydrolase activity in either the whole cell preparation or the sonicate, aliquots of both whole cell suspensions and sonic disrupted suspensions are assayed by incubating 5 µl. portions of said suspensions with solutions containing 20 µl of a 1.586 mg./ml. solution of N-acetylthienamycin in 10 mM potassium phosphate buffer, pH 7 and 10 µl 0.2 M potassium phosphate buffer, pH 7.4. Controls containing antibiotic and buffer alone and also cell suspensions without antibiotic are also run. After incubation of these mixtures overnight at 28° C., 2 µl aliquots are removed and applied on cellulose coated thin layer chromatography (TLC) plates, and the TLC plates developed in EtOH:H$_2$O, 70:30. After air drying, the TLC plates are placed on a *Staphylococcus aureus* ATCC 6538P assay plates for 5 minutes. The TLC plates are removed and the assay plates incubated overnight at 37° C.

The assay plates are prepared as follows: An overnight growth of the assay organism, *Staphylococcus aereus* ATCC 6538P, in nutrient broth plus 0.2% yeast extract is diluted with nutrient broth, plus 0.2% yeast extract to a suspension having 60% transmittance at a wavelength of 660 nm. This suspension is added to Difco nutrient agar supplemented with 2.0 g./l. Difco yeast extract at 47° C. to 48° C., to make a composition containing 33.2 ml. of the suspension per liter of agar. Forty ml. of this suspension is poured into 22.5 cm.×22.5 cm. petri plates, and these plates are chilled and held at 4° C. until used (5 day maximum).

Activity of N-acetylthienamycin amidohydrolase in the incubation mixtures is indicated by the presence of a bioactive area of R$_f$ 0.44–0.47 due to thienamycin. The unreacted bioactive N-acetyl thienamycin appears at R$_f$ 0.7–0.89. The process of this Example provides one with the ability to isolate N-acetylethanolamine amidohydrolase producing microorganisms with N-acetylthienamycin amidohydrolase activity.

EXAMPLE 2

Deacetylation of N-Acetylthienamycin

A 1% (w/v) suspension of fertile lawn soil is prepared by suspending 1 g. of lawn soil in 100 ml. sterile phosphate buffer-saline solution wherein the phosphate buffer-saline solution has the following composition:

| Phosphate Buffer-Saline Solution | |
|---|---|
| NaCl | 8.8 g. |
| 1M Phosphate Buffer, pH 7.5* | 10 ml. |
| Distilled H$_2$O | 1000 ml. |

*1M Phosphate Buffer, pH 7.5
16 ml. 1M KH$_2$PO$_4$ are mixed with 84 ml. 1M K$_2$HPO$_4$. The pH of the phosphate buffer is adjusted to 7.5 by adding small quantities of either 1M KH$_2$PO$_4$ or 1M K$_2$HPO$_4$.

Aliquots of this 1% stock soil suspension are used to prepare 10×, 100× and 1,000× dilutions.

One-ml. portions of the stock suspension or 1-ml. portions of the 10×, 100× and 1,000× dilutions are added to 2-ml. portions of sterile, 1.0% agar solutions at 48° C. The mixtures are quickly poured over the surface of sterile petri dishes of 85 mm. diameter containing 20 ml. of Medium A. Medium A has the following composition:

| Medium A | |
| --- | --- |
| KH$_2$PO$_4$ | 3.0 g. |
| K$_2$HPO$_4$ | 7.0 g. |
| MgSO$_4$ | 0.1 g. |
| Distilled H$_2$O | 1000 ml. |
| N-Acetylethanolamine solution* | 8.5 ml. |

*N-Acetylethanolamine Solution
N-acetylethanolamine is diluted 10x in H$_2$O and membrane sterilized. This solution is added after autoclaving.

For solid media: Add 20 g. agar The petri dishes are incubated for 18 days at 28° C. A well-isolated colony is picked and streaked on a petri dish containing Medium B. Medium B has the following composition:

| Medium B | |
| --- | --- |
| Tomato paste | 40 g. |
| Ground oatmeal | 15 g. |
| Distilled H$_2$O | 1000 ml. |
| pH adjusted to 6 using NaOH | |

For solid media: Add 20 g. agar An individual clone is selected and grown for 2 days at 28° C. on a slant of Medium B. A portion of the growth on this slant is streaked on the surface of six slants prepared from Medium B. These slants are incubated for 2 days at 28° C. This culture was identified as *Protaminobacter ruber* and has been designated MB-3528 in the culture collection of MERCK & CO., Inc., Rahway, New Jersey.

A portion of the growth on the slant of *Protaminobacter ruber* MB-3528 is used to inoculate a 250-ml. Erlenmeyer flask containing 50 ml. of Medium C. Medium C has the following composition:

| Medium C | |
| --- | --- |
| Dextrose | 20 g. |
| Pharmamedia | 8 g. |
| Corn Steep Liquor (wet basis) | 5 g. |
| Distilled H$_2$O | 1000 ml. |
| pH adjusted to 7 with NaOH or HCl | |
| N-Acetylethanolamine solution* | 8.5 ml. |

*N-Acetylethanolamine Solution
N-acetylethanolamine is diluted 10x in H$_2$O and membrane sterilized. This solution is added after autoclaving.

The flask is shaken at 28° C. on a 220 rpm (2" throw) shaker for 4 days. A 25-ml. portion from the flask is centrifuged for 15 minutes at 8,000 rpm. The supernatant is removed and the cells on the surface of the media solids scraped off into 0.5 ml. 0.05 M potassium phosphate buffer, pH 7.4. The resulting suspension is subjected to ultrasonic disruption using a Branson Instrument Model LS-75 Sonifier with a ½ inch probe at setting B 4 for 4, 15-second intervals, while chilling the suspension in ice water during and between disruption. A 10-μl portion of the sonicate is mixed with a 25-μl solution containing 840 μg/ml. of N-acetylthienamycin in 10 mM potassium phosphate buffer, pH 7 and incubated overnight at 28° C. Controls containing antibiotic and buffer alone; and sonicated cells and buffer without atibiotic are also run. After incubation overnight at 28° C., 2-μl quantities are applied on cellulose coated TLC plates, which are developed in EtOH:H$_2$O, 70:30. After air drying, the TLC plate is placed on a *Straphyloccus aureus* ATCC 6538P assay plate for 5 minutes.

The assay plates are prepared as follows: An overnight growth of the assay organism, *Staphylococcus aureus* ATCC 6538P, in nutrient broth plus 0.2% yeast extract is diluted with nutrient broth, plus 0.2% yeast extract to a suspension having 60% transmittance at a wavelength of 660 nm. This suspension is added to Difco nutrient agar supplemented with 2.0 g./l. Difco yeast extract at 47° C. to 48° C. to make a composition containing 33.2 ml. of the suspension per liter of agar. Forty ml. of this suspension is poured into 22.5 cm.×22.5 cm. petri dishes, and these plates are chilled and held at 4° C. until used (5 day maximum).

The TLC plate is removed and the assay plate incubated overnight at 37° C. In addition to the unreacted bioactive N-acetylthienamycin spot at R$_f$ 0.70–0.89, a bioactive spot is observed at R$_f$ 0.44–0.47 due to thienamycin. Control incubation mixtures of antibiotic plus buffer, cell sonicate plus buffer, and antibiotic plus buffer to which cell sonicate is added just prior to TLC application produce no bioactive material at R$_f$ 0.44–0.47.

EXAMPLE 3

Deacetylation of 890A$_1$

A portion of the growth on the slant of *Protaminobacter ruber* MB-3528 is used to inoculate a 250 ml. Erlenmeyer flask containing 50 ml. of Medium C. Medium C has the following composition:

| Medium C | |
| --- | --- |
| Dextrose | 20 g. |
| Pharmamedia | 8 g. |
| Corn Steep Liquor (wet basis) | 5 g. |
| Distilled H$_2$O | 1000 ml. |
| pH adjusted to 7 with NaOH or HCl | |
| N-Acetylethanolamine solution* | 8.5 ml. |

*N-Acetylethanolamine Solution
N-acetylethanolamine is diluted 10x in H$_2$O and membrane sterilized. This solution is added after autoclaving.

The flask is shaken at 28° C. on a 220 rpm (2" throw) shaker for 4 days. A 25-ml. portion from the flask is centrifuged for 15 minutes at 8,000 rpm. The supernatant is removed and the cells on the surface of the media solids scraped off into 0.5 ml. 0.05 M potassium phosphate buffer, pH 7.4. The resulting suspension is subjected to ultrasonic disruption using a Branson Instrument Model LS-75 Sonifier with a ½ inch probe at setting 4 for 4, 15 second intervals, while chilling the suspension in ice water during and between disruption. A 10-μl portion of the sonicate is mixed with 25 μl of an 890A$_1$ solution containing 4.85 hydroxylamine-extinguishable optical density units at 300 nm/ml. Controls containing antibiotic and buffer alone; and sonicated cells and buffer without antibiotic are also run. After incubation overnight at 28° C., 5 μl quantities are applied on a cellulose coated TLC plate, which is developed in EtOH:H$_2$O, 70:30. After air drying, the TLC plate is placed on a *Staphylococcus aureus* ATCC 6538P assay plate for 5 minutes.

The assay plates are prepared as follows: An overnight growth of the assay organism, *Staphylococcus*

*aureus* ATCC 6538P, in nutrient broth plus 0.2% yeast extract is diluted with nutrient broth, plus 0.2% yeast extract to a suspension having 60% transmittance at a wavelength of 660 nm. This suspension is added to Difco nutrient agar supplemented with 2.0 g./l. Difco yeast extract at 47° C. to 48° C., to make a composition containing 33.2 ml. of the suspension per liter of agar. Forty ml. of this suspension is poured into 22.5 cm.×22.5 cm. petri plates, and these plates are chilled and held at 4° C. until used (5 day maximum).

The TLC plate is removed and the assay plate incubated overnight at 37° C. In addition to the unchanged bioactive 890$A_1$ spot at $R_f$ 0.7–0.89, a new bioactive spot is observed at $R_f$ 0.44–0.47 due to desacetyl 890$A_1$. Control incubation mixtures of antibiotic plus buffer, and cell sonicate plus buffer produce no bioactive material at $R_f$ 0.44–0.47.

EXAMPLE 4

Deacetylation of 890$A_3$

Antibiotic 890$A_3$ is deacetylated by the process described in Example 3 for the deacetylation of 890$A_1$ to provide desacetyl 890$A_3$.

EXAMPLE 5

Preparation of desacetyl 890$A_1$

Six 250-ml. Erlenmeyer seed flasks containing 50 ml. each Medium C are inoculated with a portion of a slant of *Protaminobacter ruber* MB-3528. Medium C has the following composition:

| Medium C | |
|---|---|
| Dextrose | 20 g. |
| Pharmamedia | 8 g. |
| Corn Steep Liquor (wet basis) | 5 g. |
| Distilled $H_2O$ | 1000 ml. |
| pH adjusted to 7 with NaOH or HCl | |
| N-Acetylethanolamine solution* | 8.5 ml. |

*N-Acetylethanolamine Solution
N-acetylethanolamine is diluted 10x in $H_2O$ and membrane sterilized. This solution is added after autoclaving.

The flasks are shaken at 28° C. on a 220 rpm (2" throw) shaker for 1 day.

Forty-one 2-liter production flasks containing 400 ml. Medium C each are inoculated with 7 ml. per flask of the growth from these seed flasks. These production flasks are shaken at 28° C. on a 220 rpm shaker (2" throw) for 6 days. The contents of the flasks are pooled and centrifuged at 8,000 rpm for 15 minutes. The cells are scraped off the media solids pellet into a final volume of 1,600 ml. 0.05 M potassium phosphate buffer, pH 7.4. This suspension is again centrifuged at 8,000 rpm for 15 minutes. The cells are scraped off the media solids pellet into a final volume of 160 ml. 0.05 M potassium phosphate buffer, pH 7.4. This suspension is chilled to 5° C. and aliquots of 15 ml. each are exposed to successive 15 second cycles of ultrasonic irradiation, employing the equipment described in Example 1, until no further diminution of turbidity is observed when a 500× dilution is made of the suspension into phosphate buffer-saline wherein the phosphate buffer-saline solution has the following composition:

| Phosphate Buffer-Saline Solution | |
|---|---|
| NaCl | 8.8 g. |
| 1M Phosphate Buffer, pH 7.5* | 10 ml. |
| Distilled $H_2O$ | 1000 ml. |

*1M Phosphate Buffer, pH 7.5
16 ml. 1M $KH_2PO_4$ are mixed with 84 ml. 1M $K_2HPO_4$. The pH of the phosphate buffer is adjusted to 7.5 by adding small quantities of either 1M $KH_2PO_4$ or 1M $K_2HPO_4$.

To 1 liter of 0.005 M potassium phosphate buffer, pH 7.4, are added 250 mg. of the antibiotic 890$A_1$. To this mixture is added 160 ml. of the sonic extract of *Protaminobacter ruber* containing N-acetylthienamycin amidohydrolase. The mixture is stirred slowly with a magnetic stirrer at 28° C. for 20 hours. The mixture is then centrifuged at 10,000 g. for 15 minutes and the supernatant removed, chilled to 5° C., and adjusted to pH 4.5±0.2 by the addition of acetic acid. Separation of desacetyl 890$A_1$ from the unhydrolyzed antibiotic and from other constituents of the reaction mixture is effected in the following manner, a disc-diffusion bioassay against *Staphylococcus aureus* ATCC 6538P and measurements of hydroxylamine-extinguishable absorbance at 297 nm being used to monitor the performance of the purification procedures. (As described in Assay Procedures for Thienamycin).

The acidified, centrifuged reaction mixture is absorbed at the rate of 12 ml./min. on a 120 ml. bed of Dowex 50 × 4 sodium cycle, 20–50 mesh resin. The adsorbate is washed with 120 ml. of deionized water and then eluted with 2% aqueous pyridine at 6 ml./min. Following the emergence of 75 ml. of the latter eluant from the column, the succeeding 240 ml. are pooled and concentrated to 25 ml. and the concentrate adjusted to pH 7.

The 25 ml. concentrate is adsorbed at a rate of 1 ml./min. on a 25 ml. bed of Dowex-1×2, 50–100 mesh, chloride cycle resin. The resin is eluted with deionized water at the same rate. Following the emergence of 25 ml. of the eluant from the column, the succeeding 50 ml. are pooled, neutralized to pH 7 and concentrated to 10 ml. This concentrate is adjusted to pH 6.3 with acetic acid and is applied to a bed of Dowex 50×8 (200–400 mesh) resin in the 2,6-lutidinium cycle, having a diameter of 1 cm. and height of 50 cm., which had previously been equilibrated with 0.1 M 2,6-lutidine acetate buffer, pH 6.3. Elution is conducted with the buffer at the rate of 1 ml./min. Following the emergence of 25 ml. of the eluant from the column, the succeeding 35 ml. are pooled and freeze-dried.

The freeze-dried solids are dissolved in 0.5 ml. of 0.1 M 2,6-lutidine acetate buffer, pH 7.0. The solution is applied to a column of Bio-Gel P-2 (200–400 mesh), having a diameter of 1 cm. and height of 50 cm., which had previously been equilibrated with this buffer. The gel is then developed with the same buffer at a rate of 0.5 ml./min. Following the emergence of 25 ml. of eluant from the column, the succeeding 10 ml. are pooled and freeze-dried.

The freeze-dried solids are dissolved in 4 ml. distilled water and applied on a 1.7 cm. diameter column packed with 90 ml. prewashed XAD-2 and equilibrated at 5° C. with distilled water. The XAD-2 is washed prior to use successively with (1) 5 volumes of 1 N NaOH followed by deionized $H_2O$ until effluent is neutral; (2) 5 volumes 1 N HCl followed by deionized $H_2O$ until the effluent is neutral; (3) 5 volumes each of methanol, acetone, 0.001

N EDTA tetrasodium, and finally, distilled $H_2O$. The sample is followed by two, 2-ml. portions of distilled water. The column is developed with distilled water at the rate of 2 ml./min. Four ml. fractions of eluate are collected. Fractions 25 through 58 are pooled and lyophilized to yield desacetyl 890$A_1$.

EXAMPLE 6

Preparation of N-Acetylthienamycin by Fermentation

A tube of lyophilized culture of *Streptomyces cattleya* NRRL 8057 is opened aseptically and the contents suspended in 0.8 ml. of sterile Davis salts having the following composition:

| Davis Salts | |
| --- | --- |
| Sodium citrate | 0.5 g. |
| $K_2HPO_4$ | 7.0 g. |
| $KH_2PO_4$ | 3.0 g. |
| $(NH_4)_2SO_4$ | 1.0 g. |
| $MgSO_4 . 7H_2O$ | 0.1 g. |
| Distilled $H_2O$ | 1000 ml. |

This suspension is used to inoculate four slants of Medium A (plus agar) having the following composition:

| Medium A | |
| --- | --- |
| Yeast Autolysate (Ardamine*) | 10.0 g. |
| Glucose | 10.0 g. |
| Phosphate Buffer+ | 2.0 ml. |
| $MgSO_4 . 7H_2O$ | 0.05 g. |
| Distilled $H_2O$ | 1000 ml. |
| pH adjusted to 6.5 using NaOH | |

*Ardamine: Yeast Products Corporation
+Phosphate Buffer Solution

| | |
| --- | --- |
| $KH_2PO_4$ | 91.0 g. |
| $Na_2HPO_4$ | 95.0 g. |
| Distilled $H_2O$ | 1000 ml. |

For Slants: add agar—25.0 g./l. The inoculated slants are incubated for one week at 28° C. and then stored at 4° C.

Ten ml. of Medium A (without agar) is transferred aseptically to one of these slants, the spores and aerial mycelia scraped into suspension, and 1.2 ml. of this suspension used to inoculate three 2-liter baffled Erlenmeyer flasks containing 500 ml. of Medium A (without agar). These seed flasks are shaken at 28° C. on a 160 rpm shaker for 24 hours at which time the growth is satisfactory.

The growth from these seed flasks is pooled and used to inoculate a 756-liter stainless steel fermentor containing 467 liters of Medium A (without agar). This tank is operated at 28° C. using an agitation rate of 130 rpm and an airflow of 10 cu. ft. per minute for 24 hours. Defoamer, Polyglycol 2000 (Dow Chemical Corp.), is used as required but does not exceed 0.1%. pH determinations are made as follows:

| Age, Hours | 0 | 24 |
| --- | --- | --- |
| pH | 6.3 | 6.4 |

Four hundred fifty-four liters of the growth in this seed tank is used to inoculate a 5,670-liter stainless steel fermentor containing 4,082 liters of Medium E, wherein Medium E has the composition:

| Medium E | |
| --- | --- |
| Cerelose | 25.0 g. |
| Corn Steep Liquor (wet basis) | 15.0 g. |
| Distiller's Solubles | 10.0 g. |
| Cottonseed Media (Pharmamedia) | 5.0 g. |
| $CoCl_2 . 6H_2O$ | 0.01 g. |
| $CaCO_3$ (after pH adjustment) | 3.0 g. |
| Polyglycol 2000 | 0.25% |
| Tap water | 1000 ml. |
| pH adjusted to 7.3 using NaOH | |

This tank is run at 24° C. using an agitation rate of 70 rpm and an airflow of 54.3 cu. ft. per minute for 138 hours. Additional defoamer, Polyglycol 2000, is added as required, but does not exceed 0.1%. Antibacterial assays are run and the data is as follows:

| Age | pH | ATCC No. 6633 (⅜" disc.) (mm.) |
| --- | --- | --- |
| 0 | 6.9 | 0 |
| 24 | 6.3 | 0 |
| 36 | 6.0 | 0 |
| 48 | 5.9 | 0 |
| 60 | 6.0 | 23 |
| 72 | 5.9 | — |
| 84 | 6.0 | 21 |
| 96 | 6.2 | — |
| 108 | 6.5 | 35 |
| 120 | 6.6 | 36 |
| 132 | 6.7 | 41 |
| 138 | 6.7 | 39 |

The 4082 liters of fermentation broth is filtered using a 30-inch filter press and a filter aid admix to the extent of 4% w/v. A 46 g. amount of ethylenedinitrile tetraacetic acid (EDTA), sodium salt is added to the filtrate. The filtrate is cooled to 6° C., adjusted to pH 4.5±0.2 and maintained at 6° C. The cold filtrate is applied to a 480 liter column of Dowex 50×4 $Na^+$, 20–50 mesh at about 48 l./minute. After a 1400 liter forerun has passed through, 18.9 liters of spent is collected, the pH of the spent is adjusted to 7.08 with NaOH, and stored at 5° C.

A 3.8-cm. diameter column packed with 300 ml. of Dowex 1×2, 50–100 mesh, resin in the chloride cycle is prepared and washed with 600 ml. of deionized water at 5° C. Four liters of the cold Dowex 50×4 spent is passed through the column at the rate of 30 ml./minute. The column is washed with 300 ml. 25 μM EDTA. The antibiotic, N-acetylthienamycin, is eluted at 5° C. at the rate of 15 ml./minute with 900 ml. 5% NaCl solution containing 0.01 M potassium phosphate buffer, pH 7.0, and 25 μM EDTA. Fourteen fractions of 75 ml. are collected and assayed for biological activity by the disc-diffusion procedure. Eluate fractions 3 through 9, comprising 525 ml. are pooled and concentrated under vacuum to 115 ml. The concentrate contains 65% of the total bioactive material applied on the Dowex 1×2 $Cl^-$ column.

The Dowex 1×2 $Cl^-$ eluate concentrate is applied at 5° C. on a 3.8 cm. diameter column packed with 450 ml. prewashed XAD-2. The XAD-2 is prewashed columnwise successively with 4 column volumes:

(1) 0.001 M EDTA, (2) 1 N NaOH, (3) deionized $H_2O$, (4) 1 N HCl, (5) deionized $H_2O$, (6) methanol, (7) acetone, (8) deionized water and prior to use with 2250 ml. 5% NaCl solution containing 25 μM EDTA.

After the sample is applied to the column, it is followed by two 25-ml. portions of H$_2$O. The column is developed at 5° C. with deionized H$_2$O at a flow rate of 10 ml./minute. The first fraction contains 400 ml. and 11 additional fractions of 75 ml. are collected. The pH of each fraction is adjusted to between 6.9 and 7.13 with 1 N NaOH or 1 N HCl Fractions 3 to 9, containing 46% of the total bioactive material applied to the XAD-2 column, are combined and have a total volume of 490 ml. A sample of 45 ml. is removed for bioassays by the standard disc-diffusion procedure against *Staphylococcus aureus* ATCC 6538P. The remaining 445 ml. is concentrated under vacuum to 50 ml.

The 50 ml. XAD-2 eluate concentrate is pumped at 5° C. onto a 1.5 cm. column packed with 40 ml. prewashed Dowex 1×4 Cl$^-$, minus 400, at 5° C. and at a rate of 1 ml./min. The Dowex 1×4 Cl$^-$, minus 400 (defined by decanting from water) resin is washed column-wise prior to use with 240 ml. 0.2 M NaCl containing 0.005 M NH$_4$Cl and 0.1 mM NH$_4$OH at the rate of 1 ml./minute and then with 120 ml. deionized water at the same rate.

After the sample is applied to the column, it is followed by two, 5-ml. portions of deionized water. The column is developed at 5° C. at the rate of 0.92 ml./min. with 0.07 M NaCl containing 0.005 M NH$_4$Cl and 0.1 mM NH$_4$OH. Fractions of 8.6 to 9.3 ml. are collected. Fractions obtained after 600 ml. of eluate have been collected and ending with 710 ml. are pooled and contain 98% of the total bioactive material applied on the Dowex 1×4 column. This pool is concentrated under vacuum to 2 ml.

The Dowex 1×4 concentrate is applied to a 2.2 cm. diameter column packed with 225 ml. Bio-Gel P-2, 200–400 mesh, with an exclusion limit of 1800 Daltons (defined prior to use by decantation from distilled water).

The Bio-Gel P-2 column is washed prior to use with 225 ml. 1 M NaCl followed by 100 ml. deionized water. The column is developed with 5° C. deionized water at the rate of 1 ml./minute, and two ml. fractions are collected. Fractions from 104 ml. to 128 ml. eluate, containing 83% of the bioactivity applied to the Bio-Gel P-2 column, are combined and concentrated to 1.58 ml.

A 50 ml. XAD-2 column (1.6 cm.×27 cm.) is prepared and prewashed column-wise with 200 ml. of 1 mM EDTA, 1 N NaOH, deionized water, 1 N HCl, deionized water, methanol, acetone, and deionized water. The Bio-Gel P-2 concentrate containing 44.4 hydroxylamine-extinguishable optical density units is applied to the XAD-2 column at 5° C. and is followed by two, 2-ml. portions of deionized water. The column is washed with deionized water at the rate of 1 ml./minute until the UV absorbance at 300 nm of the washings is reduced to 0.060. The column is eluted with 50% methanol in deionized water at the rate of 1 ml./minute and 1-ml. fractions are collected. Fractions having absorbance at 300 nm over 0.1 are combined and concentrated under vacuum to give the product, N-acetylthienamycin containing 11.6 hydroxylamine-extinguishable O.D. units.

EXAMPLE 7

Preparation of N-Acetylthienamycin by Fermentation

A tube of lyophilized culture of *Streptomyces cattleya* MA-4297 is opened aseptically and the contents suspended in 0.8 ml. of sterile Davis salts having the following composition:

| Davis Salts | |
|---|---|
| Sodium citrate | 0.5 g. |
| K$_2$HPO$_4$ | 7.0 g. |
| KH$_2$PO$_4$ | 3.0 g. |
| (NH$_4$)$_2$SO$_4$ | 1.0 g. |
| MgSO$_4$ . 7H$_2$O | 0.1 g. |
| Distilled H$_2$O | 1000 ml. |

This suspension is used to inoculate four slants of Medium A (plus agar) having the following composition:

| Medium A | |
|---|---|
| Yeast Autolysate (Ardamine*) | 10.0 g. |
| Glucose | 10.0 g. |
| Phosphate Buffer+ | 2.0 ml. |
| MgSO$_4$ . 7H$_2$O | 0.05 g. |
| Distilled H$_2$O | 1000 ml. |
| pH adjusted to 6.5 using NaOH | |

*Ardamine: Yeast Products Corporation
+Phosphate Buffer Solution

| | |
|---|---|
| KH$_2$PO$_4$ | 91.0 g. |
| Na$_2$HPO$_4$ | 95.0 g. |
| Distilled H$_2$O | 1000 ml. |

For Slants: add agar—25.0 g./l.

The inoculated slants are incubated for one week at 28° C. and then stored at 4° C.

Ten ml. of Medium A is transferred aseptically to one of these slants, the spores and aerial mycelia scraped into suspension, and 1.2 ml. of this suspension used to inoculate three 2-liter baffled Erlenmeyer flasks containing 500 ml. of Medium A (without agar). These seed flasks are shaken at 28° C. on a 160 rpm shaker for 24 hours at which time the growth is satisfactory.

The growth from these seed flasks is pooled and used to inoculate a 756 liter stainless steel fermentor containing 467 liters of Medium A (without agar). This tank is operated at 28° C. using an agitation rate of 130 rpm and an airflow of 10 cu. ft. per minute for 24 hours. Defoamer, Polyglycol 2000 (Dow Chemical Corp.), is used as required but does not exceed 0.1%. pH determinations are made as follows:

| Age, Hours | 0 | 24 |
|---|---|---|
| pH | 6.3 | 6.4 |

Four hundred fifty-four liters of the growth in this seed tank is used to inoculate a 5,670 liter stainless steel fermentor containing 4,082 liters of Medium E, wherein Medium E has the composition:

| Medium Medium E | |
|---|---|
| Cerelose | 25.0 g. |
| Corn Steep Liquor (wet basis) | 15.0 g. |
| Distiller's Solubles | 10.0 g. |
| Cottonseed Media (Pharmamedia) | 5.0 g. |
| CoCl$_2$ . 6H$_2$O | 0.01 g. |
| CaCO$_3$ (after pH adjustment) | 3.0 g. |
| Polyglycol 2000 | 0.25% |
| Tap water | 1000 ml. |
| pH adjusted to 7.3 using NaOH | |

This tank is run at 24° C. using an agitation rate of 70 rpm and an airflow of 54.3 cu. ft. per minute for 138 hours. Additional defoamer, Polyglycol 2000, is added as required, but does not exceed 0.1%. Antibacterial assays are run and the data is as follows:

| Age | pH | ATCC No. 6633 (⅜" disc.) (mm.) |
| --- | --- | --- |
| 0 | 6.9 | 0 |
| 24 | 6.3 | 0 |
| 36 | 6.0 | 0 |
| 48 | 5.9 | 0 |
| 60 | 6.0 | 23 |
| 72 | 5.9 | — |
| 84 | 6.0 | 21 |
| 96 | 6.2 | — |
| 108 | 6.5 | 35 |
| 120 | 6.6 | 36 |
| 132 | 6.7 | 41 |
| 138 | 6.7 | 39 |

The 4082 liters of fermentation broth is filtered using a 30-inch filter press and a filter aid admix to the extent of 4% w/v. A 46 g. amount of ethylenedinitrile tetraacetic acid (EDTA), sodium salt is added to the filtrate. The filtrate is cooled to 6° C., adjusted to pH 4.5±0.2 and maintained at 6° C. The cold filtrate is applied to a 480 liter column of Dowex 50×4 Na+, 20–50 mesh at about 48 l./minute. After a 1400 liter forerun has passed through, 18.9 liters of spent is collected, the pH of the spent is adjusted to 7.08 with NaOH, and stored at 5° C.

A 3.8 cm. diameter column packed with 300 ml. of Dowex 1×2, 50–100 mesh, resin in the chloride cycle is prepared and washed with 300 ml. of deionized water at 5° C. Four liters of the cold Dowex 50×4 spent is passed through the column at the rate of 30 ml./minute. The column is washed with 350 ml. 25 μM EDTA and then eluted at 5° C. with 900 ml., 5% NaCl solution containing 0.01 N Tris.HCl, pH 7, and 25 μM EDTA at the rate of 15 ml./minute. Fractions of 75 ml. are collected and assayed by the disc-diffusion procedure against *Staphylococcus aureus* ATCC 6538P. Fractions 4 to 10 containing 47% of the bioactivity applied are added to 42.5 ml. of the sample removed for bioassay from the first XAD-2 pool described in Example 6. These combined fractions are concentrated under vacuum to 100 ml., and the pH adjusted to 6.32 with HCl.

A 3.8-cm. diameter column packed with 450 ml. XAD-2 resin is prewashed column-wise successively with 4 column volumes: (1) 0.001 M EDTA, (2) 1 N NaOH, (3) deionized H₂O, (4) 1 N HCl, (5) deionized H₂O, (6) methanol, (7) acetone, (8) deionized water and washed prior to use with 2250 ml. 5% NaCl solution containing 25 μM EDTA. The above concentrate is applied to the XAD-2 column and is followed by two, 5-ml. portions of deionized water. The column is developed at 5° C. at the rate of 10 ml./minute with deionized water. The first fraction contains 40 ml., and subsequent fractions of 75 ml. are collected and assayed by the disc-diffusion process. Fractions 9 to 15, containing 22% of the bioactivity applied on the XAD-2 column are pooled and concentrated under vacuum to 56 ml.

A 21 cm.×1.7 cm. column packed with 40 ml. of Dowex 1×4 Cl⁻, minus 400 mesh, (defined by decanting from water) is washed column-wise prior to use with 240 ml. 0.2 M NaCl containing 0.005 M NH₄Cl and 0.1 mM NH₄OH at the rate of 1 ml./minute and then with 120 ml. deionized water at the same rate.

The XAD-2 concentrate is applied on the column and is followed by two, 2-ml. portions of deionized water and then by two, 2-ml. portions of eluting buffer. The column is eluted at 5° C. with a solution 0.07 M NaCl containing 0.005 M NH₄Cl and 0.1 mM NH₄OH at the rate of 1 ml./minute. Fractions of 10 ml. are collected and assayed by the disc diffusion method. Eluate fractions from 544 ml. through 647 ml. containing an apparent 100% of the applied bioactivity are combined and concentrated under vacuum to 2.3 ml. The concentrate contains 36.4 hydroxylamine-extinguishable optical density units.

A 2.2 cm.×62 cm. column packed with 225 ml. Bio-Gel P-2, 200–400 mesh resin with an exclusion limit of 1800 Daltons is washed prior to use with 225 ml. 1 M NaCl followed by 100 ml. deionized water. The Dowex 1×4 concentrate is applied to the column and is followed by two, 2-ml. portions of deionized water. The column is developed at 5° C. with deionized water at the rate of 1 ml./minute and 2 ml. fractions are collected and assayed by the disc-diffusion procedure. Fractions from 124 ml. to 129 ml., containing 7.04 hydroxylamine-extinguishable O.D. units are combined and concentrated under vacuum to 2 ml. to give an aqueous solution of the product, N-acetylthienamycin. Fractions from 117 to 123 ml. and 130 to 139 ml. are combined to give a solution of the product, N-acetylthienamycin containing 13.7 hydroxylamine-extinguishable O.D. units. Deacetylation of this material obtained herewith in accordance with the process of Example 2 affords the antibiotic thienamycin.

EXAMPLE 8

Preparation of Thienamycin

A tube of lyophilized culture of *Streptomyces cattleya* MA-4297 is opened aseptically and the contents suspended in 50 ml. of sterile Medium A contained in a 250-ml. baffled Erlenmeyer flask. Medium A has the following composition:

| Medium A | |
| --- | --- |
| Yeast Autolysate (Ardamine*) | 10.0 g. |
| Glucose | 10.0 g. |
| Phosphate Buffer+ | 2.0 ml. |
| MgSO₄ . 7H₂O | 0.05 g. |
| Distilled H₂O | 1000 ml. |
| pH adjusted to 6.5 using NaOH | |

*Ardamine: Yeast Products Corporation
+Phosphate Buffer Solution

| | |
| --- | --- |
| KH₂PO₄ | 91.0 g. |
| Na₂HPO₄ | 95.0 g. |
| Distilled H₂O | 1000 ml. |

The inoculated flask is shaken at 28° C. on a 220 rpm (2" throw) for 48 hours. Forty ml. of the 48-hour broth is removed aseptically and mixed with 40 ml. of sterile 20% (v/v) aqueous glycerol. Two-ml. quantities of the resulting mixture are pipetted into sterile 1-gram vials which are then frozen and stored in the vapor phase of a liquid nitrogen freezer.

Frozen vial contents are used to inoculate a 250 ml. baffled Erlenmeyer flask containing 50 ml. of Medium A. This seed flask is shaken at 28° C. on a 160 rpm shaker at 28° C. for 24 hours.

Ten-ml. portions from this seed flask are used to inoculate 2-liter baffled Erlenmeyer flasks containing 500 ml. of Medium A. These seed flasks are shaken on a 160 rpm shaker at 28° C. for 24 hours.

A one thousand-ml. portion of the pooled contents of these seed flasks is used to inoculate a 756-liter stainless steel fermentor containing 467 liters of Medium A. This tank is operated at 28° C. using an agitation rate of 130 rpm and an airflow of 10 cu. ft. per minute for 24 hours. Polyglycol 2000 (Dow Chemical Corp.) is used as required as a defoamer but not to exceed 0.1%. Measurements of pH and dextrose are made and are as follows:

| Age: Hours | 0 | 12 | 24 |
|---|---|---|---|
| pH | 6.4 | 6.4 | 6.6 |
| Dextrose mg./ml. | 8.1 | 8.1 | 8.1 |

Four hundred fifty-three liters of this growth are used to inoculate a 5670-liter stainless steel fermentor containing 4082 liters of Medium E, wherein Medium E has the composition:

| Medium E | |
|---|---|
| Cerelose | 25.0 g. |
| Corn Steep Liquor (wet basis) | 15.0 g. |
| Distiller's Solubles | 10.0 g. |
| Cottonseed Media (Pharmamedia) | 5.0 g. |
| $CoCl_2 \cdot 6H_2O$ | 0.01 g. |
| $CaCO_3$ (after pH adjustment) | 3.0 g. |
| Polyglycol 2000 | 0.25% |
| Tap water | 1000 ml. |
| pH adjusted to 7.3 using NaOH | |

This tank is operated at 24° C. using an agitation rate of 70 rpm and an airflow of 54.3 cu. ft. per minute for 144 hours. Defoamer, Polyglycol 2000, is added as required but does not exceed 0.1%. Centrifuged broth is assayed against *Staphylococcus aureus* ATCC 6538P by the standard disc-diffusion procedure. The results are tabulated in the table below under the heading "Antibiotic Activity vs ATCC 6538P". Assays are also run by the disc-diffusion procedure using 3/8-inch filter-paper discs and 10 ml. assay plates and the results tabulated in the table below under the heading "Antibiotic Activity (10 ml. plates)".

The 10 ml. assay plates are prepared as follows: An overnight growth of the assay organism, *Staphylococcus aureus* ATCC 6538P, in nutrient broth plus 0.2% yeast extract is diluted with nutrient broth plus 0.2% yeast extract to a suspension having 40% transmittance at a wavelength of 660 mµ. This suspension is added to Difco nutrient agar supplemented with 2.0 g./l. Difco yeast extract, at 47° C. to 48° C., to make a composition containing 33.2 ml. of the suspension per liter of agar. Ten ml. of this suspension are poured into petri plates of 85 mm. diameter, and the plates are chilled and held at 4° C. until used (5 day maximum).

| Age | pH | Dextrose mg./ml. | Antibiotic Activity vs ATCC 6538P (mm.) | Antibiotic Activity (10 ml. plates) (mm.) |
|---|---|---|---|---|
| 0 | 6.6 | 22.2 | | |
| 12 | 6.3 | 20.2 | | |
| 24 | 5.8 | 18.0 | | 0 |
| 36 | 6.0 | 13.2 | | 21.5 |
| 48 | 6.0 | 8.6 | | 21.5 |
| 60 | 5.7 | 6.4 | | 26.5 |
| 72 | 5.8 | 2.7 | | 25.5 |
| 84 | 6.2 | 0.3 | | 27.5 |
| 96 | 6.4 | 0.2 | | 36.0 |
| 108 | 6.4 | 0 | | 35.0 |
| 120 | 6.3 | | 41.5 | 37.0 |
| 132 | 5.8 | | | 37.5 |
| 144 | 5.9 | | 43.0 | 37.5 |

The 4082 liters of fermentation broth is filtered using a 30-inch filter press and a filter aid admix to the extent of 4% w/v. A 12 g. amount of (ethylenelinitrilo) tetraacetic acid, sodium salt is added to the filtrate. The filtrate is cooled to 6° C., adjusted to pH 4.5±0.2 and maintained at 6° C. The cold filtrate is adsorbed on 480 l. of Dowex 50×4 Na+, 20–50 mesh at about 48 l./min. The adsorbate is washed with 480 l. of deionized water and then eluted with 2% aqueous pyridine at 24 l./min. and three fractions of 300 l., 520 l. and 240 l. are collected and assayed at pH 7.0. The assays indicate that the eluate fractions contain 4%, 16% and 6%, respectively of the bioactivity applied on the Dowex 50×4 Na+ column. Eluate fraction two is concentrated to 48 l. and adjusted to pH 7.

The 48 l. concentrate is adjusted to pH 7.3 and adsorbed on 76 l. of Dowex 1×2, 50 to 100 mesh, chloride cycle resin at 7.6 l./min. The resin is eluted with deionized water at the same rate. Four fractions are collected, two of 48 l., one of 70 l. and one of 48 l. The fractions are adjusted to pH 7 as collected. Assays indicate that 68% of the starting bioactivity is in the 70 l. fraction. This fraction is concentrated to 18 l. at pH 7.0 and filtered using a 0.45 micron Millipore Filter. The filtrate is tray freeze-dried to yield 99 grams of product having a potency of 310 units/mg.

Ten g. of the freeze-dried solids are taken up in 0.1 M 2,6-lutidine acetate buffer, pH 6.3. The solution, 125 ml. readjusted to pH 6.3 with acetic acid, is applied to a column of Dowex 50×8 (200–400 mesh) in the 2,6-lutidine cycle, 7.6×142 cm., which had previously been equilibrated with buffer, and developed with 0.1 M buffer at 25 ml./min. A 3-l. fore-cut is collected followed by 200 fractions of 20 ml. each. Every fourth fraction 36 through 192 is assayed at a dilution of 1:200. The bioactivity is contained in fractions 56 through 192, reaching a maximum in fractions 92 through 96. Fractions 80 through 136 are combined and 590 ml. of deionized water added to give 1760 ml. The pooled, diluted, solution containing 62% of the starting bioactivity applied on the Dowex 50×8 column, is freeze-dried.

The freeze-dried solids are dissolved in 0.1 M 2,6-lutidine acetate, pH 7.0 buffer. The solution, 27 ml., is applied to a column of Bio-Gel P-2 (200–400 mesh) 5×112 cm. which had previously been equilibrated with 0.1 M buffer. The gel is then developed with the same buffer at 10 ml./min.

The effluent stream is monitored with a Meccomatic recording differential refractometer. The development is continued until 105 fractions, 20 ml. each, are collected. Every fraction, 70 through 93, is assayed at a dilution of 1:300. The bio-activity is found in fractions 73 through 82, reaching a maximum in fractions 77 and 78. Fractions 75 through 80 are freeze-dried to obtain 90 mg. of antibiotic with an average potency of 10,000 units/mg.

The 90 mg. of freeze-dried solid is taken up into 4 ml. of 0.01 M potassium phosphate buffer, pH 7. This solution, containing 596 hydroxylamine-extinguishable optical density units (this measure of the thienamycin content being described in Section II of *Assay Procedures for Thienamycin*) is applied on a 1.7-cm. diameter column packed with 90 ml. prewashed XAD-2 and equilibrated prior to use with 180 ml. of 0.01 M potassium phosphate buffer, pH 7, at 5° C. The XAD-2 is washed prior to use successively with (1) 5 volumes of 1 N NaOH followed by deionized $H_2O$ until effluent is neutral; (2) 5 volumes 1 N, —followed by deionized $H_2O$ until the effluent is neutral; (3) 5 volumes each of methanol, acetone, 0.001 M EDTA tetrasodium, and finally distilled $H_2O$. Vacuum is applied to all solvents before use.

After the sample is applied on the column it is followed by two, 2-ml. portions of the phosphate buffer. The column is developed at 5° C. with the buffer at a flow rate of 2 ml./min. Four-ml. fractions of eluate are collected. Fractions obtained after 100 ml. of eluate has been collected and ending with 253 ml. are combined and concentrated on a rotary evaporator under vacuum and below 10° C. to a volume of 6 ml.

This solution, containing 436 hydroxylamine-extinguishable optical density units, is applied on a 1.7 cm. diameter column packed with 90 ml. XAD-2 prewashed as above and equilibrated at 5° C. with distilled water. The sample is followed by two, 2-ml. portions of distilled water. The column is developed with distilled water at the rate of 2 ml./min. Four-ml. fractions of eluate are collected. Fractions obtained after 100 ml. of eluate has been collected and ending with 151 ml. are pooled and concentrated on a rotary evaporator to a volume of 2.73 ml. and the solution lyophilized to yield 6.49 mg. of thienamycin. Fractions obtained between 152 ml. and 345 ml. are pooled and concentrated on a rotary evaporator to a volume of 3.34 ml. and lyophilized to yield 11.53 mg. of thienamycin. These fractions contain a total of 369 hydroxylamine-extinguishable optical density units. This represents a 3.1 fold purification over the material applied to the first XAD-2 column and yields a calculated potency of 31,000 units/mg. Spectrophotometric analysis of a sample of this product shows an $E_{1\ cm.}^{1\%} = 253$ when measured in phosphate buffer, pH 7, at 297 nm.

A ten-g. portion of the 99 g. freeze-dried solids obtained by the Dowex 1×2 purification above is taken up in 0.1 M 2,6-lutidine acetate buffer, pH 6.3. The solution, 125 ml., readjusted to pH 6.3 with acetic acid, is applied to a 7.6×142 cm. column of Dowex 50×8 in the 2,6-lutidine cycle, which had previously been equilibrated with buffer. The column is developed with 0.1 M buffer at 35 ml./min. A 3.6-1. fore-cut is collected followed by 200 fractions of 20 ml. each. Every fourth fraction 6 through 194 is assayed at a dilution of 1:200. The bioactivity is contained in fractions 18 through 178, reaching a maximum in fractions 62 through 82. Fractions 42 through 102 are combined and 640 ml. of deionized water added to give 1920 ml. The pooled, diluted, solution containing 63% of the bio-activity applied on the Dowex 50×8 column, is freeze-dried.

The freeze-dried solids are dissolved in 0.1 M 2,6-lutidine acetate, pH 7.0 buffer. The solution, 25 ml., is applied to a 5×112 cm. column of Bio-Gel P-2 (200–400 mesh), which had previously been equilibrated with 0.1 M buffer. The gel is then developed with the same buffer at 10 ml./min.

The effluent stream is monitored with a Meccomatic recording differential refractometer. The development is continued until 125 fractions, 20 ml. each, are collected. Every fraction, 70 through 89, is assayed at a dilution of 1:300. The bio-activity is found in fractions 72 through 81, reaching a maximum in fraction 77. Fractions 75 through 79 are freeze-dried to obtain 100.5 mg. of antibiotic with a potency of 8320 units/mg.

The 100.5 mg. of freeze-dried solid is taken up into 4 ml. of 0.01 M potassium phosphate buffer, pH 7. This solution, containing 692 hydroxylamine-extinguishable optical units is applied on a 1.7-cm. diameter column packed with 90 ml. prewashed XAD-2 and equilibrated prior to use with 180 ml. of 0.01 M potassium phosphate buffer, pH 7, at 5° C. The XAD-2 is washed prior to use successively with (1) 5 volumes of 1 N NaOH followed by deionized $H_2O$ until effluent is neutral; (2) 5 volumes 1 N HCl followed by deionized $H_2O$ until the effluent is neutral; (3) 5 volumes each of methanol, acetone, 0.001 M EDTA tetrasodium, and finally distilled $H_2O$. Vacuum is applied to all solvents before use.

After the sample is applied on the column it is followed by two 2-ml. portions of the phosphate buffer. The column is developed at 5° C. with the buffer at a flow rate of 2 ml./min. Four-ml. fractions of eluate are collected. Fractions obtained after 109 ml. of eluate has been collected and ending with the 309th ml. are combined. To this combined eluate is added the 11.53-mg. sample of XAD-2 purified antibiotic obtained above comprising 186 hydroxylamine-extinguishable optical density units. The combined eluate together with the added antibiotic is concentrated in vacuo on a rotary evaporator at a temperature below 10° C. to a volume of 7 ml.

This solution, containing 720 hydroxylamine-extinguishable optical density units is applied on a 1.7-cm. diameter column packed with 90 ml. XAD-2 prewashed as above and equilibrated at 5° C. prior to use with distilled water. The sample is followed by two, 2-ml. portions of distilled water. The column is developed with distilled water at the rate of 2 ml./min. Four-ml. fractions of eluate are collected. Fractions obtained after 109 ml. of eluate have been collected and ending with the 301st ml. are pooled and concentrated on a rotary evaporator to a volume of 10.3 ml. This solution, containing 589 hydroxylamine-extinguishable optical density units, is lyophilized to yield 23.6 mg. of antibiotic with a calculated potency of 30,140 units/mg.

The antibiotic thienamycin thus prepared is a white, amorphous solid with a fibrous consistency, a sample of which on exposure in a glass capillary tube to temperatures elevated at a rate of 3° C. per minute, underwent decomposition without the intervention of a liquid phase in the following stages: softening occurred at 130° to 140° C. with a contraction in volume of the solid continuing until 170° to 174° C. in which range the material yellowed; sintering and a progressive intensification of color to reddish-brown being observed in the range 180° to 200° C. and finally carbonization and residual traces of solid being found at 205° C.

A further sample of this material on spectrophotometric analysis shows an absorbance peak at 296.5 nm with an $E_{1\ cm.}^{1\%} = 268.2$. Elemental analysis yields the following results: (1) a 5.67% weight loss upon drying at room temperature for 4 hours under vacuum, and (2) the composition 47.68% carbon, 6.22% hydrogen, 11.48% nitrogen. These results are consistent with the empirical formula $C_{11}H_{16}N_2O_4S \cdot (NH_3)_{0.28}$, the calculated elemental composition corresponding to this empirical formula being C=47.68%; H=6.13%, N=11.52%, S=11.57% and O=23.1%. Polarimetric analysis of a 1 mg./ml. solution of this sample in 10 mM potassium phosphate buffer showed a specific optical rotation $[\alpha]_D^{27°}$ C.+80. The infrared spectrum of a nujol mull of this sample revealed characteristic absorption peaks at 1765 cm.$^{-1}$, 1650-1550 cm.$^{-1}$, 2800-2500 cm.$^{-1}$, and 3500-3100 cm.$^{-1}$. An NMR spectrum at 100 MHz of a sample of this product dissolved in O$_2$O reveals a doublet at $\delta$1.275, a pair of doublets at $\delta$3.39 and multiplets at $\delta$3.15 and $\delta$4.20, these peaks being characteristic of thienamycin.

The thienamycin obtained herewith may be acetylated according to the process of Example 8 to afford N-acetylthienamycin.

EXAMPLE 9

Acetylation of Thienamycin

Thienamycin, 10.9 mg. is stirred for 10 minutes at 0° C. in 1 ml. dry DMF plus 2 ml. freshly prepared acetic anhydride. The DMF and acetic anhydride are removed by washing repeatedly (5 to 6 times) with 25–40-ml. portion of hexane and one last portion of hexane after the addition of 1 ml. dry ethyl ether. The crude sample of N-acetylthienamycin is dissolved in 20 ml. of deionized water which contains 100 μmoles of Tris base [tris(hydroxymethyl)aminomethane] and 35 μmoles of HCl. The pH, after dissolution of the sample, is 7.9. The solution contains 244 absorbance units at 298 nm and a ½ inch assay disc containing 0.1 ml. of a 1000 fold dilution, produces a 23 mm. zone of inhibition when incubated on ATCC 8461 plates at 25° C.

This sample is applied on a column (1.3 cm.×14 cm. bed dimensions) of Dowex-1×4 (Cl$^-$) minus 400 mesh. The column is washed with 10 ml. of deionized water and the antibiotic, N-acetylthienamycin, is eluted with 0.07 M NaCl+0.005 M NH$_4$Cl+0.0001 M NH$_3$ is deionized water. Fractions of 6.1 ml. are collected at a flow rate of 0.7 ml. per minute. The main peak of UV absorbance at 298 nm appears in fractions 36 through 50, with a maximum at fraction 40. Fractions 38 through 46 are combined, containing a total of 107 absorbance units at 298 nm. The combined fractions are rotary evaporated under reduced pressure to 2 ml. and 5 μl of 1 M NaOH is added.

This concentrate is applied on a column (2.2×80 cm. bed dimensions) of Bio-Gel P-2, 200–400 mesh. The sample is washed in with two, 1-ml. portions of deionized water and eluted with deionized water at a flow rate of 0.6 ml. per minute. Fractions of 3.04 ml. are collected.

The main peak of UV absorbance at 300 nm appears in fractions 58 through 64, with a maximum at fraction 60. Fractions 59 through 62 containing 83.7 A$_{300}$ units are pooled. A portion equivalent to 2.2 A$_{300}$ units is removed for reference, and the remainder is concentrated to 1.5 ml. and lyophilized in a 14 ml. glass vial to give 3.9 mg. of N-acetylthienamycin.

$\lambda_{max}$ 301 nm, $E_{max}/E_{min}$=4.45, E%$_{301}$ in deionized water=208.

Deacetylation of this starting material in accordance with the process of Example 2 affords the antibiotic thienamycin.

EXAMPLE 10

Preparation of Antibiotic 890A$_3$

A tube of lyophilized culture of *Streptomyces flavogriseus* MA-4434a is opened aseptically and the contents suspended in a tube containing 0.8 ml. of sterile Davis salts having the following composition:

| Davis Salts | |
|---|---|
| Sodium citrate | 0.5 g. |
| K$_2$HPO$_4$ | 7.0 g. |
| KH$_2$PO$_4$ | 3.0 g. |
| (NH$_4$)$_2$SO$_4$ | 1.0 g. |
| MgSO$_4$ . 7H$_2$O | 0.1 g. |
| Distilled H$_2$O | 1000 ml. |

This suspension is used to inoculate four slants of Medium A having the following composition:

| Medium A | |
|---|---|
| Glycerol | 20.0 g. |
| Primary Yeast | 5.0 g. |
| Fish Meal | 15.0 g. |
| Distilled H$_2$O | 1000 ml. |
| Agar | 20.0 g. |
| pH adjusted to 7.2 using NaOH | |

The inoculated slants are incubated for one week at 27°–28° C. and then stored at 4°–6° C. until used (not longer than 21 days).

Ten ml. of Medium B having the composition:

| Medium B | |
|---|---|
| Yeast Autolysate (Ardamine *) | 10.0 g. |
| Glucose | 10.0 g. |
| Phosphate Buffer+ | 2.0 ml. |
| MgSO . H$_2$O | 50 mg. |
| Distilled H$_2$O | 1000 ml. |
| pH adjusted to 6.5 using HCl or NaOH | |

*Ardamine: Yeast Products Corporation
+Phosphate Buffer solution

| KH$_2$PO$_4$ | 91.0 g. |
|---|---|
| Na$_2$HPO$_4$ | 95.0 g. |
| Distilled H$_2$O | 1000 ml. | is transferred aseptically to one of these slants, the spores and aerial mycelia scraped into suspension, and 3.3 ml. of this suspension used to inoculate a 2-liter baffled Erlenmeyer flask containing 500 ml. of Medium B. This seed flask is shaken at 28° C. on a 160 rpm shaker (2" throw) for 36 hours at which time the growth is satisfactory.

The growth from this seed flask is used to inoculate a 189-liter stainless steel seed tank containing 160 liters of Medium B. This tank is operated at 28° C. using an agitation rate of 150 rpm and an airflow of 3 cu. ft. per minute for 24 hours. Defoamer, Polyglycol 2000 (Dow Chemical Corp.), is used as required but not to exceed 0.1%. pH determinations are made as follows:

| Age, Hours | 0 | 12 |
|---|---|---|
| pH | 6.3 | 6.35 |

Forty-three liters of the growth in this seed tank is used to inoculate a 756-liter stainless steel fermentor containing 467 liters of Medium C, wherein Medium C has the composition:

| Medium C | |
|---|---|
| Tomato Paste | 20.0 g. |
| Primary Yeast | 10.0 g. |

-continued

| Medium C | |
|---|---|
| Dextrin (Amidex) | 20.0 g. |
| CoCl$_2$ . 6H$_2$O | 5.0 mg. |
| Distilled H$_2$O | 1000 ml. |
| pH adjusted to 7.2–7.4 using NaOH | |

This tank is run at 25° C. using an agitation rate of 146 rpm and an airflow of 9 cu. ft. per minute for 92 hours. Additional defoamer, Polyglycol 2000, is added as required, not to exceed a 0.1%. Antibacterial assays are run on *Salmonella gallinarum MB*-1287, *Vibrio percolans* ATCC 8461 and the data is as follows:

| Age, Hours | 0 | 12 | 24 | 36 | 48 | 60 | 72 | 84 | 92 |
|---|---|---|---|---|---|---|---|---|---|
| pH | 6.6 | 6.7 | 6.65 | 6.3 | 6.0 | 6.4 | 6.15 | 6.5 | 6.5 |
| MB-1287 mm. | — | — | — | S | — | 19 | 26 | 28 | 32 |
| ATCC 3461 mm. (1–10) | — | — | | S | — | 21 | 24 | 26 | 30 |
| 890A units/ml. | | | | NA | NA | 6.8 | 13.5 | 24.9 | 24.3 |

The 890A units/ml. are determined as set forth in Section II of Assay Procedures for Antibiotics 890A$_1$ and 890A$_3$.

One hundred twenty-five gallons of broth is chilled to 5° C. and centrifuged through a Titan P-9 centrifuge. Fifty pounds of Celite is added to the 100 gallons of supernatant, and the suspension filtered through a Shriver 18-inch filter press. The 91 gallons of filtrate is adsorbed on a column containing seven gallons of Dowex-1×2 (Cl$^-$), 50–100 mesh, and the column washed with 10 gallons of deionized water. The mixture of antibiotics 890A$_1$ and 890A$_3$ is eluted with thirty gallons of 5% NaCl+0.01 M Tris HCl buffer, pH 7.0+25 $\mu$M neutral EDTA in deionized water. Fractions of 5 gallons each are collected. The mixture of antibiotics 890A$_1$ and 890A$_3$ appears in fractions 3 through 6, with peak potency in fractions 4 and 5. Fractions 4, 5, and 6, containing 8% of the activity of the filtered broth, are combined and concentrated under reduced pressure to 2 gallons.

The two gallons of concentrate are applied to a column containing 10 gallons of XAD-2 which had been previously washed with 50 gallons of 60% aqueous acetone followed by 50 gallons of deionized water and 50 gallons of 5% NaCl solution. The concentrate is eluted with 37.5 gallons of deionized water. Three fractions of 2.5 gallons followed by six fractions of five gallons are collected. The activity appears in fractions 1 through 6, with a peak of potency in fraction 3. Fractions 4 and 5, containing 64% of the activity applied to the XAD column, or 370,000 units are pooled.

Fractions 4 and 5 are concentrated to 120 ml. by evaporation under reduced pressure. The pH is adjusted to 6.5 and the concentrate is applied to a column (7×50 cm.) of XAD-2 which had been washed with 8 liters of 60% aqueous acetone followed by 4 liters of deionized water and 8 liters of 5% NaCl in deionized water. The sample is drained to bed level and the column rinsed with three 20-ml. portions of deionized water, draining to bed level each time. The antibiotic is then eluted with seven liters of deionized water at a flow rate of 40 ml. per minute. Eight fractions of 200 ml. followed by fourteen fractions of 400 ml. are collected. Antibiotic activity appears in fractions 4 through 19, containing 77% of the bioactivity applied on the column (as measured by the *Salmonella gallinarum MB*-1287 assay), with a peak of activity in fractions 6 through 8.

The ratio of bioactivity of the fractions on *Vibrio percolans* ATCC 8461 and the HAEA$_{300}$ for the fractions is determined. Those fractions displaying the ratio value of about 250 indicate the presence of antibiotic 890A$_1$ and those having a ratio of about 31 indicate the presence of antibiotic 890A$_3$. Accordingly, fractions 10, 11, 12 and 13, containing mostly antibiotic 890A$_3$, are combined for further processing.

Combined fractions 10 through 13 obtained from the second XAD-2 column are concentrated to 40 ml. and applied on a column (2.15 cm.×40 cm. bed dimensions) of Dowex-1×4 (Cl$^-$) minus 400 mesh. The antibiotic is eluted with three liters of 0.075 M NH$_4$Cl and 0.001 M NH$_3$ in deionized water, at a flow rate of 3 ml. per minute. Fractions of 9 ml. are collected. Antibiotic activity, assayed by *Vibrio percolans* ATCC 8461, appears in fractions 165 through 234, with a peak of activity in fractions 195 through 201.

Fractions 186 through 213 are combined, containing a total of 472 A$_{300}$ units, of which 312 were extinguishable by reaction with hydroxylamine.

These combined fractions are concentrated to 4.2 ml. by rotary evaporation under reduced pressure. The concentrate is applied to a column of Bio-Gel P-2 (200–400 mesh) with bed dimensions 2.15×60 cm. The sample is allowed to drain to bed level, and two rinses of 1 ml. each of deionized water are applied and drained to bed level. The column is eluted with deionized water at a flow rate of 1 ml. per minute, collecting fractions of 2.6 ml. each.

The antibiotic 890A$_3$ eluted in fractions 38 through 48, with a peak at fraction 41, determined by hydroxylamine-extinguishable absorbance at 300 nm. Fractions 40 through 43 are pooled, containing 260 A$_{300}$ units, of which 173 are hydroxylamine-extinguishable.

To remove residual contamination of antibiotic 890A$_3$ by antibiotic 890A$_1$, the combined desalted fractions 40 through 43 are treated wioth 50 $\mu$l. of penicillinase [Difco "Bacto-Penase" containing 500,000 units per ml. (1000 LU/ml. wherein the term LU refers to Levy units; 1,000 LU will inactivate 500,000 units of penicillin G)] and 0.1 ml. of 1 M Tris-HCl buffer, pH 7.5. The reaction is allowed to stand at 23° C. for 6 hours, and then 3 ml. of deionized water and 15 ml. of methanol is added. This mixture is applied on a column (2.15×44 cm. bed dimensions) of Dowex-1×2 (Cl$^-$) minus 400 mesh, which had been packed in 50% methanol and washed with two liters of 50% (v/v) methanol. The antibiotic 890A$_3$ is eluted with 2 liters of 0.05 M NaCl+0.005 M NH$_4$Cl+0.0001 M NH$_3$ in 50% methanol. Fractions of 9.2 ml. are collected. The main peak of UV absorbance, measured at 300 nm, occurs in fractions 74 through 88. Fractions 78 through 85 are pooled. The total absorbance units at 300 nm in these fractions, after removal of the methanol by evaporation under reduced pressure, is 97.6, of which 87.5 are extinguishable by reaction with hydroxylamine.

The pooled fractions 70 through 85 are concentrated to 3.92 ml. by rotary evaporation under reduced pressure, and the concentrate applied on a column of Sephadex G-10 (2.15×70 cm. bed dimensions) which had been washed with 4 ml. of 4 M NH$_3$, followed by equilibration with 0.15 mM NH$_3$ in deionized water. After two washes of 1 ml. each of 0.02 mM NH$_3$, the antibiotic 890A$_3$ is eluted with 0.02 mM NH$_3$, at a flow rate of 0.8 ml. per minute. Forty-nine fractions of 2.45 ml., followed by twenty fractions of 3.33 ml. are collected. The main peak of absorbance at 300 nm appears in fractions 35 through 53. Fractions 38 through 46, having the highest $A_{300}/A_{245}$ values, are combined for further processing. The combined fraction have a total of 65 absorbance units at 300 nm. The pooled fractions are rotary evaporated under reduced pressure to 2.84 ml., and divided into two equal portions which are quick-frozen and lyophilized separately in 14 ml. glass vials to give antibiotic 890A$_3$. One sample contains 32.0 $A_{300}$ units in 0.88 mg., and the other contains 31.9 $A_{300}$ units in 0.82 mg. The former sample containing 32.0 $A_{300}$ units was subjected to NMR analysis and showed the following peaks:

1.29 (d, J=6.5); 1.98 (s); 3.42 (d of d, J=5 and J=2.4); ~4.01-4.28 (m); 3.14 (d of d, J=5 and J=9); 3.39 (t, J=6.5); 2.92 (d of t, J=~4 and J=6).

The above table lists the 100 MHz-NMR signals for 890A$_3$ sodium salt in D$_2$O relative to the internal standard, sodium 2,2-dimethyl-2-silapentane-5-sulfonate; chemical shifts are given in ppm and coupling constants in Hz; apparent multiplications are indicated.

Deacetylation of this material obtained herewith in accordance with the process of Example 4 affords the antibiotic desacetyl 890A$_3$.

EXAMPLE 11

Preparation of Antibiotic 890A$_1$

A tube of lyophilized culture of *Streptomyces flavogriseus* MA-4600a is aseptically opened and the contents suspended in a tube containing 1.5 ml. of sterile Medium A having the following composition:

| Medium A | |
|---|---|
| Yeast Extract | 10.0 g. |
| Glucose | 10.0 g. |
| MgSO$_4$ . 7H$_2$O | 0.05 g. |
| Phosphate Buffer+ | 2 ml. |
| Distilled H$_2$O | 1000 ml. |
| +Phosphate Buffer Solution | |
| KH$_2$PO$_4$ | 91.0 g. |
| Na$_2$HPO$_4$ | 950 g. |
| Distilled H$_2$O | 1000 ml. |

This suspension is used to inoculate a 250-ml. triple-baffled Erlenmeyer seed flask containing 54 ml. of seed Medium B having the following composition:

| Medium B | |
|---|---|
| Autolyzed Yeast (Ardamine*) | 10.0 g. |
| Glucose | 10.0 g. |
| MgSO$_4$ . H$_2$O | 0.05 g. |
| Phosphate Buffer+ | 2 ml. |
| Distilled H$_2$O | 1000 ml. |
| pH adjusted to 6.5 with NaOH | |
| *Ardamine: Yeast Products Corporation | |
| +Phosphate Buffer Solution | |
| KH$_2$PO$_4$ | 91.0 g. |
| Na$_2$HPO$_4$ | 950 g. |
| Distilled H$_2$O | 1000 ml. |

The seed flask is stoppered with cotton and shaken for 30 hours at 28° C.±1° C. on a 220 rpm gyrotory shaker (2" throw).

Fifty 250-ml. unbaffled Erlenmeyer production flasks, each containing 40 ml. of production Medium C are inoculated with 1 ml. per flask of the broth from the seed flask. The production flasks are stoppered with cotton.

| Medium C | |
|---|---|
| Tomato Paste | 20.0 g. |
| Primary Yeast | 10.0 g. |
| Dextrin (Amidex) | 20.0 g. |
| CoCl$_2$ . 6H$_2$O | 5.0 mg. |
| Distilled H$_2$O | 1000 ml. |
| pH adjusted to 7.2-7.4 using NaOH | |

After inoculation, the production flasks are incubated at 28° C.±1° C. with shaking on a 220 rpm gyrotory shaker (2" throw) for 3 days. The flasks are assayed for activity against standard *Vibrio percolans* ATCC 8461 assay plates using ½ inch assay discs dipped into centrifuged fermentation broth samples. Samples are diluted with 0.05 M phosphate buffer, pH 7.4. The results are tabulated below:

| Harvest Age Hours | 72 |
|---|---|
| pH | 6.4 |
| *Vibrio percolans* | |
| (1/100 Dilution) Assay | 23 mm. |
| 890 Assay, units/ml. | 103 |

The 890A units/ml. are determined as set forth in Section II of Assay Procedures for Antibiotics 890A$_1$ and 890A$_3$.

The whole broth is centrifuged in 200-ml. portions in polycarbonate bottles at 9000 rpm for 15 minutes to give 1600 ml. of combined supernatants with a potency of 104 units/ml. To this is added 0.5 ml. of neutral EDTA.

The centrifuged broth is adsorbed on a Dowex-1×2 (Cl$^-$), 50-100 mesh column, bed dimensions 3.8×22 cm., at a flow rate of 6 to 20 ml./min. The column is rinsed with 100 ml. of deionized water and eluted with 1 liter of deionized water containing 50 g. of sodium chloride, 0.02 M Tris HCl buffer, pH 7.0, and 25 µM neutral EDTA, at a flow rate of 6 ml./min. Fractions of 10 ml. are collected.

Antibiotic 890A$_1$ appears in fractions 13 through 81, with a maximum at fractions 25 to 33, counting from the first application of salt eluate. Fractions 24 through 41, having the highest bipotency/$A_{220}$ ratios, are combined for further processing. The combined fractions have a total of 29,000 units, or 17% of the applied bioactivity.

The Dowex eluate is concentrated to 10 ml., the pH is adjusted to 6.5 with dilute hydrochloric acid, and the concentrate is applied on a column of XAD-2, bed dimensions 3.3×36 cm., which had been previously washed with 2 liters each of 60% aqueous acetone, deionized water, and 5% (w/v) sodium chloride in deionized water. The sample is eluted with deionized water at a flow rate of 6 ml./min. Fractions of 40 to 260 ml. are collected.

Antibiotic activity appears in fractions 6 through 14, extending from 220 to 2560 ml. of eluted volume. The peak is at fractions 9 and 10, extending from 370 to 550 ml. of eluted volume. Fractions 9 through 12, extending from 370 to 1060 ml. of eluted volume, have the highest ratios of HAEA$_{300}$/$A_{220}$, and are combined for further processing. These fractions have 36,600 units, equal to 126% of the apparent applied activity.

The combined fractions 9 through 12 are concentrated to 100 ml. and the concentrate applied on a column of Dowex-1×4 (Cl−), minus 400 mesh, bed dimensions 2.2×41 cm., at a flow rate of 2 ml./min. The column is rinsed with 50 ml. of deionized water, and eluted with 3 liters of 0.07 M NaCl+0.005 M NH₄Cl+0.0001 M NH₃ in deionized water, at a rate of 2 ml./min. Fractions of 10.8 ml. are collected starting from the first application of eluent.

The main peak of antibiotic $890A_1$ appears in fractions 181 through 217, with a maximum at fraction 198. Fractions 186 through 210, containing a total of 114 absorption units at 300 nm., are pooled.

The pooled fractions are concentrated to 4.0 ml., and the pH is adjusted to 7.3 by addition of 16μ liter of 1 M NaOH. The concentrate is applied on a column of Bio-Gel P-2, 200–400 mesh, bed dimension 2.15×70 cm., and is washed in with 3×1 ml. washes of deionized water and eluted with deionized water at 0.96 ml./min. Fractions of 3.85 ml. are collected.

The main peak of antibiotic $890A_1$ appears in fractions 24 through 44, with a maximum at fractions 33 and 34. Fractions 27 through 38, having the highest $A_{300}/A_{245}$ ratios, are combined for lyophilization. These combined fractions have a total of 72 $A_{300}$ units.

To carry out the lyophilization, the combined fractions are concentrated to 3.0 ml. and the pH of the concentrate is adjusted to 7.5 by addition of 10μ liters of 0.1 M NaOH. The sample is divided into two portions of 1.50 ml. each, and the portions are separately quick-frozen and lyophilized from 14 ml. glass screw-cap vials. Each sample contains 1.73 mg. of $890A_1$, corresponding to 35.8 $A_{300}$ units.

Deacetylation of this material obtained herewith according to the process of Example 3 affords the antibiotic desacetyl $890A_1$.

Compositions containing desacetyl $890A_1$ and desacetyl $890A_3$, the antibiotics of this invention, and compositions containing thienamycin may be administered in several unit dosage forms as, for example, in solid or liquid orally ingestible dosage form. The composition per unit dosage, whether liquid or solid may contain from 0.1% to 99% of active material, the preferred range being from about 10 to 60%. The compositions will generally contain from about 25 mg. to about 1000 mg. by weight of the active ingredient based upon the total weight of the composition; however, in general, it is preferable to employ a dosage amount in the range of from about 250 mg. to 1000 mg. In parenteral administration the unit dosage is usually the pure compound in a slightly acidified sterile water solution or in the form of a soluble powder intended for solution. Representative formulations can be prepared by the following procedures:

| Capsules | Per Capsule |
|---|---|
| Desacetyl $890A_1$ | 400 mg. |
| Lactose, U.S.P., a sufficient quantity to fill No. 0 Capsules, approx. 475 mg. each. | |

In the above example the active compound and the diluent are mixed to produce a uniform blend, which is then filled into No. 0 hard gelatin capsules, by hand or on a suitable machine, as required. The mixing and filling is preferably done in an area having a relative humidity less than 40%.

| Tablets | Per Tablet |
|---|---|
| Desacetyl $890A_1$ | 330. mg. |
| Calcium phosphate | 192. mg. |
| Lactose, U.S.P. | 190. mg. |
| Cornstarch | 80. mg. |
| Magnesium stearate | 8. mg. |
| | 800. mg. |

In the above example, the active component is blended with the calcium phosphate, lactose and about half of the cornstarch. The mixture is granulated with a 15% cornstarch paste and rough-screened and screened again through No. 16 screens. The balance of the cornstarch and the magnesium stearate is added and the mixture is compressed into tablets, approximately ½" in diameter, each weighing 800 mg.

Alternatively, the active component is blended with the calcium phosphate, lactose and one-half the cornstarch. The mixture is "slugged" on a heavy duty press to produce compacted tablet-like masses. These are broken down to a No. 16 mesh granule. The balance of the cornstarch and the magnesium stearate are added and the mixture is compressed into tablets approximately ½" in diameter, each weighing 800 mg.

| Lyo Form (For Injection) | Per Vial |
|---|---|
| Desacetyl $890A_1$ | 25 mg. |
| Water-for-Injection, U.S.P. to make | 5 ml. |

In the above example the active component is dissolved in sufficient water-for-injection in the ratio shown. The solution is filtered through Selas candles or Millipore membrane filters to sterilize. The solution is subdivided into sterile vials. The vials and contents are frozen, and the water is aseptically removed by lyophilization. The vials containing the sterile dry solid are aseptically sealed.

To restore for parenteral administration, 5 ml. of sterile water-for-injection is added to the contents of a vial.

| Oral Liquid Forms | Per 1000 ml. |
|---|---|
| Desacetyl $890A_1$ | 1.0 g. |
| Sucrose | 600.0 g. |
| Glucose | 250.0 g. |
| Sodium Benzoate | 1.0 g. |
| Concentrated Orange Oil | 0.2 ml. |
| Purified water U.S.P. to make | 1000.0 ml. |

The sucrose and glucose are dissolved in about 400 ml. of water using heat to aid solution. This solution is cooled and sodium benzoate, followed by the concentrated orange oil added. The solution is brought to about 900 ml. volume with water and the antibiotic is added. The solution is clarified by filtration through a coarse filter.

What is claimed is:

1. A process for producing the compound desacetyl $890A_1$ having the structure:

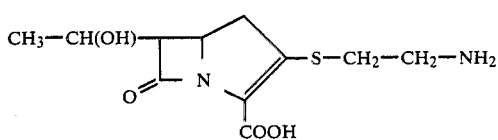

produced by enzymatic cleavage of the compound 890A₁ wherein 890A₁ has the following structure:

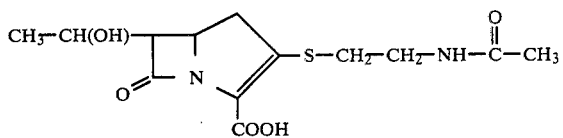

and wherein said 890A₁ has 100 MHz nuclear magnetic reasonance signals having chemical shifts in ppm and multiplicities indicated as 1.35 (d, J=6.5); 1.98 (s); 3.63 (d of d, J=5.2 and J=9.8); ~4.02-4.26 (m); 3.18 (d of d, J=2 and J=10); 3.41 (t, J=6); 2.97 (d of t, J=3.5 and J=6), wherein the enzymatic cleavage utilizes an amidohydrolase capable of hydrolyzing the N-acetyl group.

2. A process for producing the compound desacetyl 890A₃ having the structure:

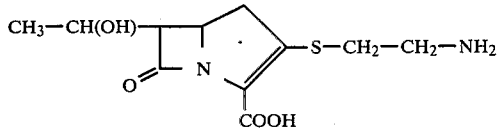

produced by enzymatic cleavage of the compound 890A₃ wherein 890A₃ has the following structure:

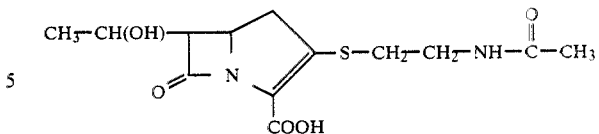

and wherein said 890A₃ has 100 MHz nuclear magnetic reasonance signals having chemical shifts in ppm and multiplicities indicated as 1.35 (d, J=6.5); 1.98 (s); 3.63 (d of d, J=5.2 and J=9.8); ~4.02-4.26 (m); 3.18 (d of d, J=2 and J=10); 3.41 (t, J=6); 2.97 (d of t, J=3.5 and J=6), wherein the enzymatic cleavage utilizes an amidohydrolase capable of hydrolyzing the N-acetyl group.

3. The process according to claim 1 wherein the amidohydrolase is an N-acetylthienamycin amidohydrolase.

4. The process according to claim 2 wherein the amidohydrolase is an N-acetylthienamycin amidohydrolase.

5. The process according to claim 1 wherein the amidohydrolase is an N-acetylethanolamine amidohydrolase.

6. The process according to claim 2 wherein the amidohydrolase is an N-acetylethanolamine amidohydrolase.

7. The process according to claim 1 wherein an amidohydrolase produced by an amidohydrolase-producing strain of the microorganism *Protaminobacter ruber* is utilized.

8. The process according to claim 2 wherein an amidohydrolase produced by an amidohydrolase-producing strain of the microorganism *Protaminobacter ruber* is utilized.

9. The process for producing thienamycin which comprises intimately contacting N-acetylthienamycin with the enzyme N-acetylthienamycin amidohydrolase produced by an amidohydrolase-producing strain of the microorganism *Protaminobacter ruber*.

10. The process for producing desacetyl 890A₁ which comprises intimately contacting 890A₁ with the enzyme N-acetylthienamycin amidohydrolase produced by an amidohydrolase-producing strain of the microorganism *Protaminobacter ruber*.

11. The process for producing desacetyl 890A₃ which comprises intimately contacting 890A₃ with the enzyme N-acetylthienamycin amidohydrolase produced by an amidohydrolase-producing strain of the microorganism *Protaminobacter ruber*.

* * * * *